US008058400B2

(12) United States Patent
Figdor et al.

(10) Patent No.: US 8,058,400 B2
(45) Date of Patent: *Nov. 15, 2011

(54) COMPOSITION AND METHOD FOR MODULATING DENDRITIC CELL-T CELL INTERACTION

(75) Inventors: Carl Gustav Figdor, Den Bosch (NL); Teunis Bernard H. Geijtenbeek, Nijmegen (NL); Yvette Van Kooyk, Arnhem (NL); Ruurd Torensma, Nijmegen (NL)

(73) Assignee: Katholieke Universiteit Nijmegen, Nijmegen (NL)

( * ) Notice: Subject to any disclaimer, the term of this patent is extended or adjusted under 35 U.S.C. 154(b) by 382 days.

This patent is subject to a terminal disclaimer.

(21) Appl. No.: 11/977,151

(22) Filed: Oct. 22, 2007

(65) Prior Publication Data
US 2008/0160041 A1 Jul. 3, 2008

Related U.S. Application Data

(62) Division of application No. 10/625,204, filed on Jul. 23, 2003, now Pat. No. 7,285,642.

(51) Int. Cl.
*C07K 16/00* (2006.01)

(52) U.S. Cl. ............... 530/387.1; 530/387.5; 530/388.1; 530/388.2; 530/388.23; 530/350; 530/389.1

(58) Field of Classification Search ........................ None
See application file for complete search history.

(56) References Cited

U.S. PATENT DOCUMENTS

| 5,989,552 A | 11/1999 | McKenzie et al. ......... 424/185.1 |
| 6,548,275 B2 | 4/2003 | Goldenberg |
| 6,605,279 B2 | 8/2003 | Freeman et al. |
| 7,148,329 B1 | 12/2006 | Figdor et al. |
| 7,285,642 B2 | 10/2007 | Figdor et al. |
| 2003/0134297 A1 | 7/2003 | Olson et al. |
| 2003/0232745 A1 | 12/2003 | Olson et al. |

FOREIGN PATENT DOCUMENTS

| WO | WO-9301820 A2 | 2/1993 |
| WO | WO-95/32734 | 12/1995 |
| WO | WO-9623882 A1 | 8/1996 |
| WO | WO-9802456 A2 | 1/1998 |
| WO | WO-9802456 A3 | 1/1998 |
| WO | WO-9828332 A2 | 7/1998 |
| WO | WO-9828332 A3 | 7/1998 |
| WO | WO-9841633 A1 | 9/1998 |
| WO | WO-9849306 A1 | 11/1998 |
| WO | WO-9855508 A2 | 12/1998 |
| WO | WO-9855508 A3 | 12/1998 |
| WO | WO-00/63251 | 10/2000 |
| WO | WO-02/50119 | 6/2002 |

OTHER PUBLICATIONS

Bakker et al. J Exp Med. Mar. 1, 1994;179(3):1005-9.
Tacken et al. Effective induction of naïve and recall T-cell responses by targeting antigen to human dendritic cells via a humanized anti-DC-SIGN antibody. Blood, 2005, 106(4): 1278-1285.
Srivastava et al. Neutralizing antibody responses to HIV: role in protective immunity and challenges for vaccine design. Expert Rev. Vaccines. 3(4) Suppl. 33-52 (2004).

Cohen. Is an Effective HIV Vaccine Feasible. Science. vol. 30. p. 99 (2005).
Sausville et al. (Cancer Research, 2006, vol. 66, pp. 3351-3354).
Johnson et al. (British J. of Cancer, 2001, 84(10):1424-1431).
Ahsan et al., Immunopathogenesis of Human Immunodeficiency Virus. Seminars in Nephrology, vol. 18, No. 4, pp. 422-435 (1998).
Fè d'Ostiani, C., et al., "Dendritic Cells Discriminate between Yeasts and Hyphae of the Fungus Candida albicans: Implications for Initiation of T Helper Cell Immunity In Vitro and In Vivo," J. Exp. Med., 191(10):1661-1673 (2000).
Forsyth, C. B., et al., "Interaction of the Fungal Pathogen Candida albicans with Integrin CD11b/CD18: Recognition by the I Domain Is Modulated by the Lectin-Like Domain and the CD18 Subunit," The Journal of Immunology, 161:6198-6205 (1998).
Fumero et al., Immunosuppressive drugs as an adjuvant to HIV treatment. Journal of Antimicrobial Chemotherapy vol. 53, pp. 415-417 (2004).
Genbank Accession No. AB015629 including updates of Apr. 17, 1999; Apr. 20, 1999; Apr. 20, 1999 (later time); Jul. 26, 2001; and Jul. 23, 2002.
Hong et al., "Human Immunodeficiency Virus Envelope (gp120) Binding to DC-SIGN and Primary Dendritic Cells Is Carbohydrate Dependent but Does Not Involve 2G12 or Cyanovirin Binding Sites: Implications for Structural Analyses of gp120-DC-SIGN Binding," Journal of Virology, 12855-12865 (2002).
Jameson et al., "Expression of DC-SIGN by Dendritic Cells of Intestinal and Genital Mucosae in Humans and Rhesus Macaques," Journal of Virology, 76:1866-1875 (2002).
Marth, T., et al., "Regulation of Interleukin-12 by Complement Receptor 3 Signaling," The Journal of Experimental Medicine, 185(11):1987-1995 (1997).
Mitchell et al., "A Novel Mechanism of Carbohydrate Recognition by the C-type Lectins DC-SIGN and DC-SIGNR," The Journal of Biological Chemistry, 276:28939-28945 (2001).
Murdoch et al., Immune reconstitution inflammatory syndrome (IRIS): review of common infections manifestations and treatment options. AIDS Research and Therapy 4:9 (2007)
Netea, M. G., et al., "Immune sensing of Candida albicans requires cooperative recognition of mannans and glucans by lectin and Toll-like receptors," The Journal of Clinical Investigation 116(6):1642-1650 (2006).

(Continued)

*Primary Examiner* — Zachariah Lucas
*Assistant Examiner* — Michelle S Horning
(74) *Attorney, Agent, or Firm* — Ropes & Gray LLP

(57) ABSTRACT

The present invention relates to the use of a compound that binds to a C-type lectin on the surface of a dendritic cell, in the preparation of a composition for modulating, in particular reducing, the immune response in an animal, in particular a human or another mammal. The composition in particular modulates the interactions between a dendritic cell and a T-cell, more specifically between a C-type lectin on the surface of a dendritic cell and an ICAM receptor on the surface of a T-cell. The compositions can be used for preventing/inhibiting immune responses to specific antigens, for inducing tolerance, for immunotherapy, for immunosuppression, for the treatment of autoimmune diseases, and the treatment of allergy. The compound that binds to a C-type lectin is preferably chosen from mannose, fucose, plant lectins, antibiotics, sugars, proteins or antibodies against C-type lectins. The invention also relates to such antibodies.

12 Claims, 14 Drawing Sheets

OTHER PUBLICATIONS

Rosati et al., Cytokine Response to Inactivated Candida albicans in Mice. Cell. Immunol., 162:256-264 (1995).
Stephen Smith. The patogenesis of HIV infection: stupid may not be so dumb after all. Retrovirology 3:60 (2006).
Soilleux, E.J., et al., "Cutting Edge: DC-SIGN; a Related Gene, DC-SIGNR; and CD23 Form a Cluster on 19p.13,1,2," The Journal of Immunology, 165:2397-2942 (2000).
Szabo, I., et al., "Modulation of Macrophage Phagocytic Activity by Cell Wall Components of Candida albicans," Cellular Immunology, 164:182-188 (1995).
Vazeux et al., "Cloning and Characterization of a New Intercellular Adhesion Molecule ICAM-R," Nature, 360:485-488, 1992.
Wu et al., "Functional Evaluation of DC-SIGN Monoclonal Antibodies Reveals DC-SIGN Interactions with ICAM-3 Do Not Promote Human Immunodeficiency Virus Type I Transmission," J. Virol., 76(12):5905-5914 (2002).
Andre et al., *Journal of Virology*, 72(2), pp. 1497-1503 (1998).
Baribaud, Frederic, et al., "Functional and Antigenic Characterization of Human, Rhesus Macaque, Pigtailed Macaque, and Murine DC-SIGN," *Journal of Virology*, 75(21), pp. 10281-10289 (2001).
Berkower, I., et al., "Chimeric HIV-1 Envelope GP120-Hepatitis B Core Antigen (HbcAg) Fusion Proteins For HIV-1 Vaccines," FASEB Journal, 10(6):A10282 (1996).
Biosis Database, PREV 197866028654 & Kataoka et al., *Cancer Research*, 38(5), pp. 1202-1207 (1987).
Cohen, *Science*, 287, p. 1567 (2000).
Curtis, BM, et al., "Sequence and Expression of a Membrane-Associated C-type Lectin that Exhibits CD4-Independent Binding of Human Immunodeficiency Virus Envelope Glycoprotein GP 120," Proc. Natl. Acad. Sci. USA 89:8356-8360 (1992).
Eck J., et al., "Cloning of the Mistletoe Lectin Gene and Characterization of the Recombinant A-Chain," European Journal of Biochemistry, 264:775-784 (1999).
Engering, Anneke, et al., "The Dendritic Cell-Specific Adhesion Receptor DC-SIGN Internalizes Antigen for Presentation to T Cells," *J. of Immun.*, 168, pp. 2118-2126 (2000).
FDA Approves Second Indication for Monolclonal Antibody, Jun. 28, 1993, printed on Nov. 12, 2004 from http://www.fda.gov/bbs/topics/ANSWERS/ANS00506.html, Jun. 28, 1993.
Feinberg, Hadar, et al., "Structural Basis for Selective Recognition of Oligosaccharides by DC-SIGN and SC-SIGNR," *Science*, 294, pp. 2163-2166 (2001) (with Supplementary Material published electronically on the *Science* website, 6 pgs.).
Geijtenbeek, et al., "Identification of Different Binding Sites in the Dendritic Cell-Specific Receptor DC-SIGN for Intercellular Adhesion Molecule 3 and HIV-1," *J. Biol. Chem.*, 227(13), pp. 11314-11320 (2002).
Geijtenbeek, Teunis, B.H., et al., "Identification of DC-SIGN, a Novel Dendritic Cell-Specific ICAM-3 Receptor that Supports Primary Immune Responses," *Cell*, pp. 575-585 (2000).
Geijtenbeek, Teunis, B.H., et al., *Cell*, pp. 587-597 (2000).
Gruber, Andreas, et al., "Functional Aspects of Binding of Monoclonal Antibody DCN46 to DC-SIGN on Dendritic Cells," *Immunology Letters*, 84, pp. 103-108 (2002).
Human CD209: anti-Human CD209 (DC-SIGN) antibody, eBioscience, http://www.ebioscience.com/ebioscience/specs/antibody_14/14-2099.htm, Jan. 5, 2004.
Janeway, Charles, A., Jr., et al., *Immunobiology*, (5th ed.), Garland Publishing, New York, p. 691 (2001).
Kataoka et al., "Potentiation of Concanavalin A-bound L1210 Vaccine in Vivo by Chemotherapeutic Agents," Cancer Research, 38:1202-1207 (1978).
Knight SC., et al., "Bone Marrow-Derived Dendritic Cells, Infection with Human Immunodeficiency Virus, and Immunopathology," Annual Review Immunology 15:593-615 (1997).
Manca F. et al., "Dendritic Cells Are Potent Antigen-Presenting Cells for In Vitro Induction of Primary Human CD4+ T-Cell Lines Specific for HIV GP 120," Journal of Acquired Immune Deficiency Syndromes 7:15-23 (1994).
Package insert for Orthoclone OKT3 Sterile Solution (murumonab-CD3) from Ortho Biotech Products LP, Raritan, NJ, Revised Mar. 2001.
Pohlmann, Stefan, et al., "DC-SIGN Interactions with Human Immunodeficiency Virus Type 1 and 2 Simian Immunodeficiency Virus," *J. of Virology9*, 75(10), pp. 4664-4672 (2001).
Product Information for Affinity Purified anti-human CD209 (DC-SIGN) antibody, from eBioscience, printed on Jan. 5, 2004 from http://www.ebioscience.com/ebioscience/specs/antibody_14/14-2099.htm.
Purified Mouse Anti-Human Monoclonal Antibody, BD PharMingen Technical Data Sheet, BD Biosciences Product Information sheet, Catalog No. 551186, May 1, 2001.
Sequence Alignment of Curtis et al., PNAS 89: 8356-8360 (1992) with SEQ ID No. 2 from U.S. Appl. No. 09/719,961.
Steinman, *Cell*, 287, pp. 491-494 (2000).
Taken, P.J., et al., "Effective induction of naive and recall T-cell responses by targeting antigen to human dendritec cells via a humanized anti-DC-SIGN antibody," Blood, 106(4):1278-1285 (2005).
Toda, et al., *Immunology*, 92, pp. 111-117 (1997).
Tsunetsugu-Yokota, Y. et al., "Efficient Virus Transmission from Dendritic Cells to CD4+ T Cells in Response to Antigen Depends on Close Contact through Adhesion Molecules," Virology 239:259-268 (1997).
Vakeva, Antti, P., et al., "Myocardial Infarction and Apoptosis After Myocardial Ischemia and Reperfusion," *Circulation*, 97, pp. 2259-2267 (1998).
Woodle, E.S., et al., Translplantation, 68, pp. 608-616 (1999).
Yan et al., "β-Glucan, a "Specific" Biologic Response Modifier That Uses Antibodies to Target Tumors for Cytotoxic Recognition by Leukocyte Complement Receptor Type 3 (CD11b/CD18)," The Journal of Immunology, 163(6):3045-3052 (1999).
Zoeteweij, JP. et al., "HIV-Dendritic Cell Interatcions Promote Efficient Viral Infection of T Cells," Journal of Biomedical Science 5:253-259 (1998).
Steinbrook R., "One Step Forward, Two Steps Back—Will There Ever Be an AIDS Vaccine?," New England Journal Med 357(26):2653-2655 (2007).
deRepentigny et al., Acquired Immunity in Experimental Murine Aspergillosis Is Mediated by Macrophages, Infect. Immun. 61(9):3791-3802 (1993).

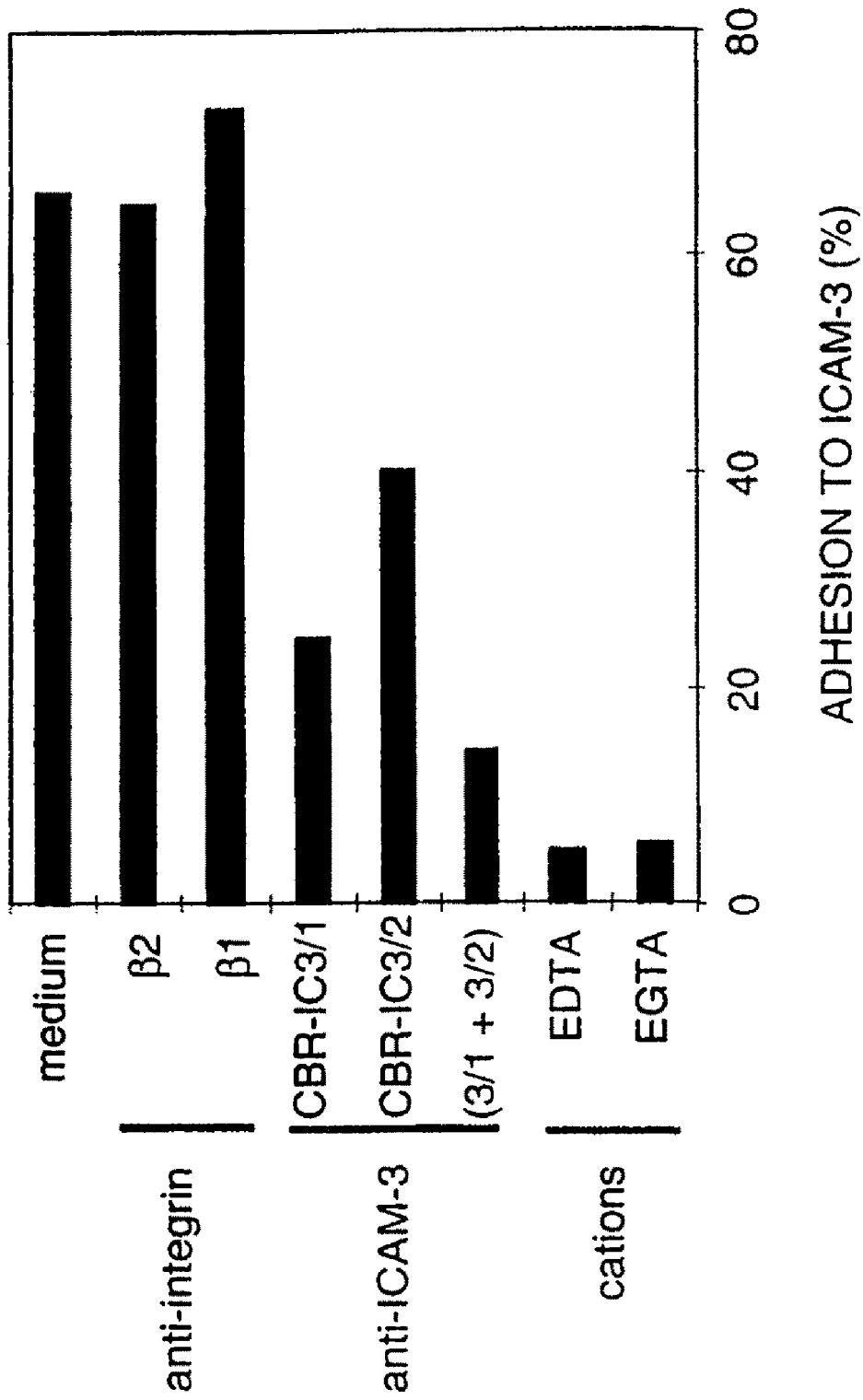

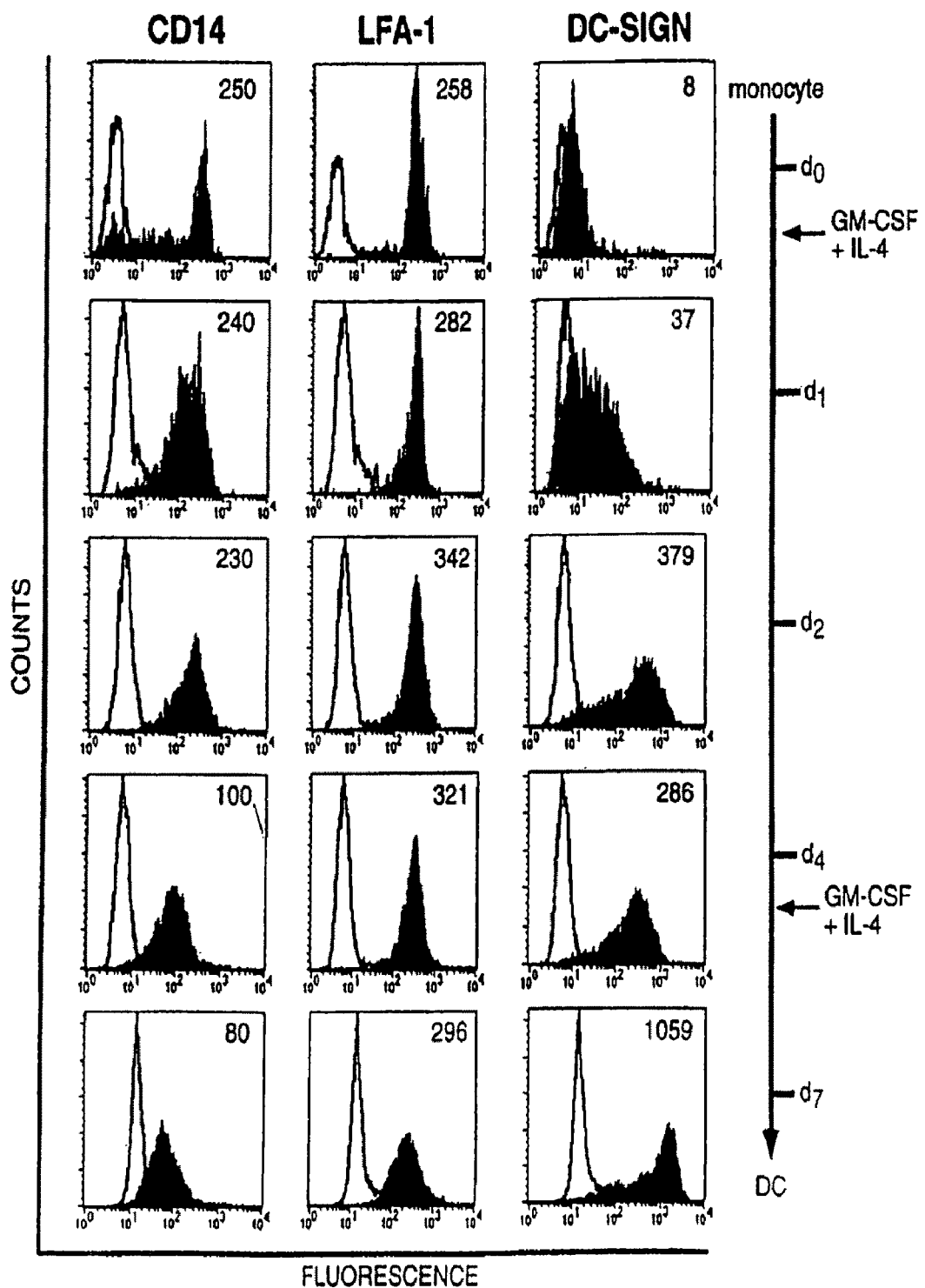

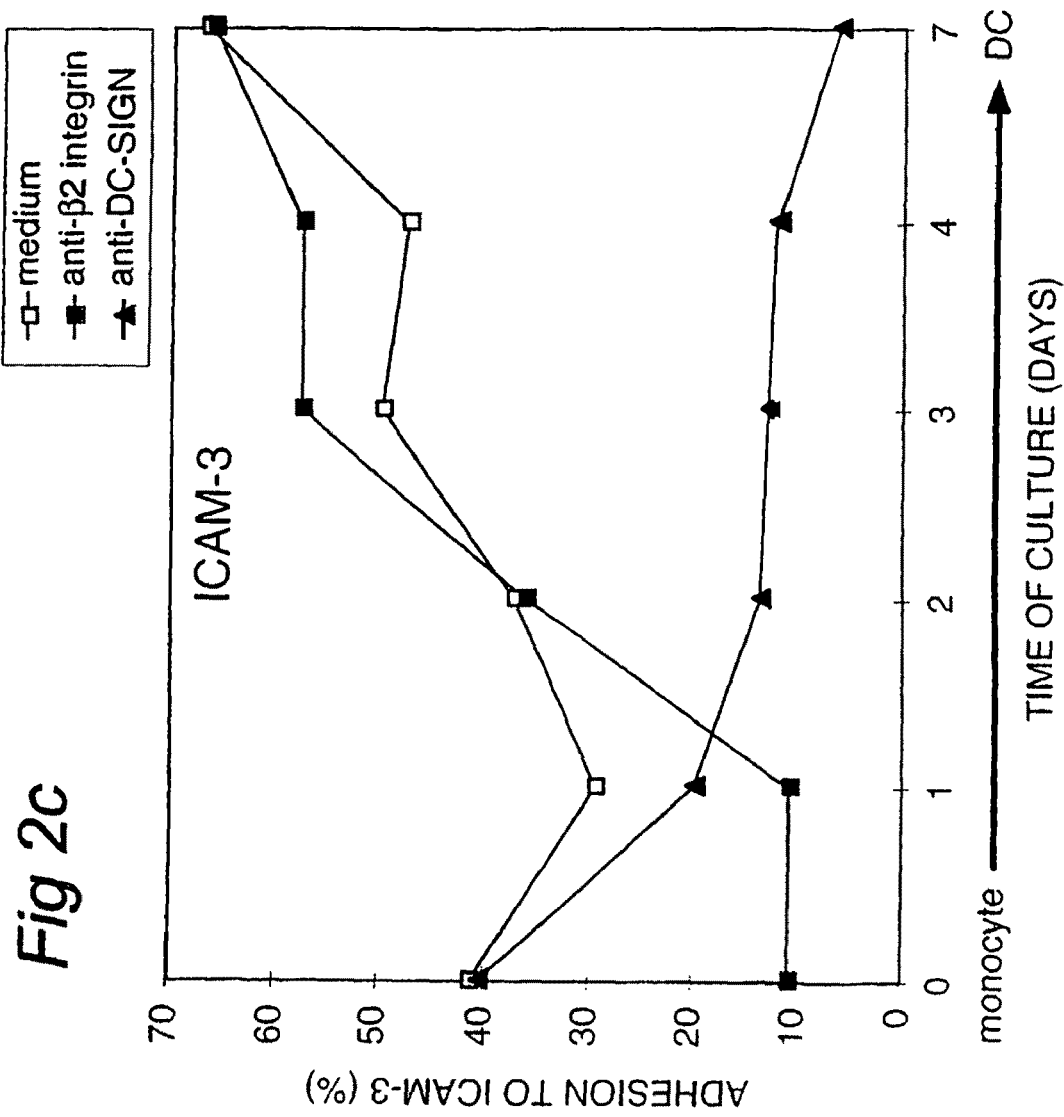

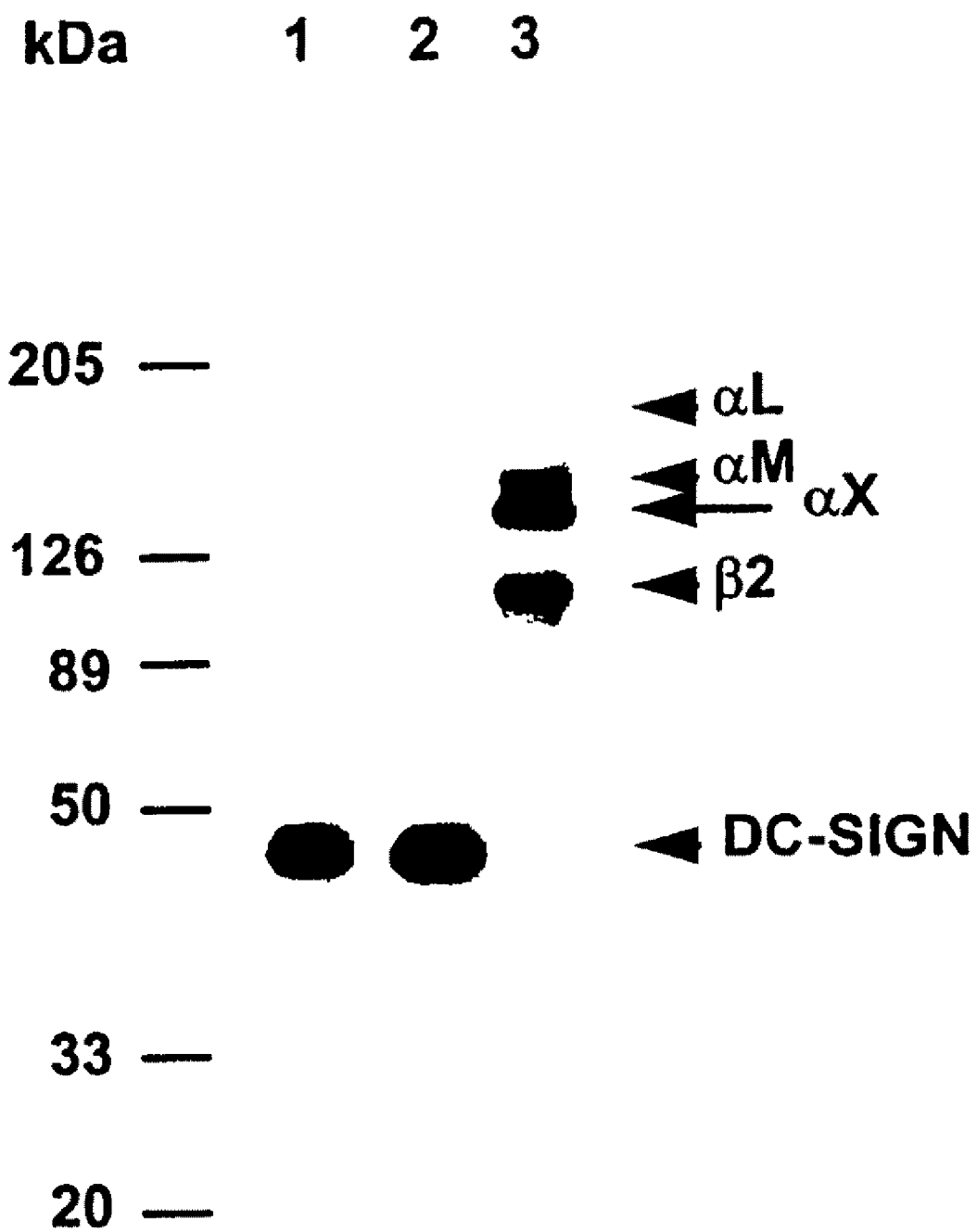

- ■ TRANSMEMBRANE REGION
- ■ REPEAT
- ▨ C-TYPE LECTIN DOMAIN

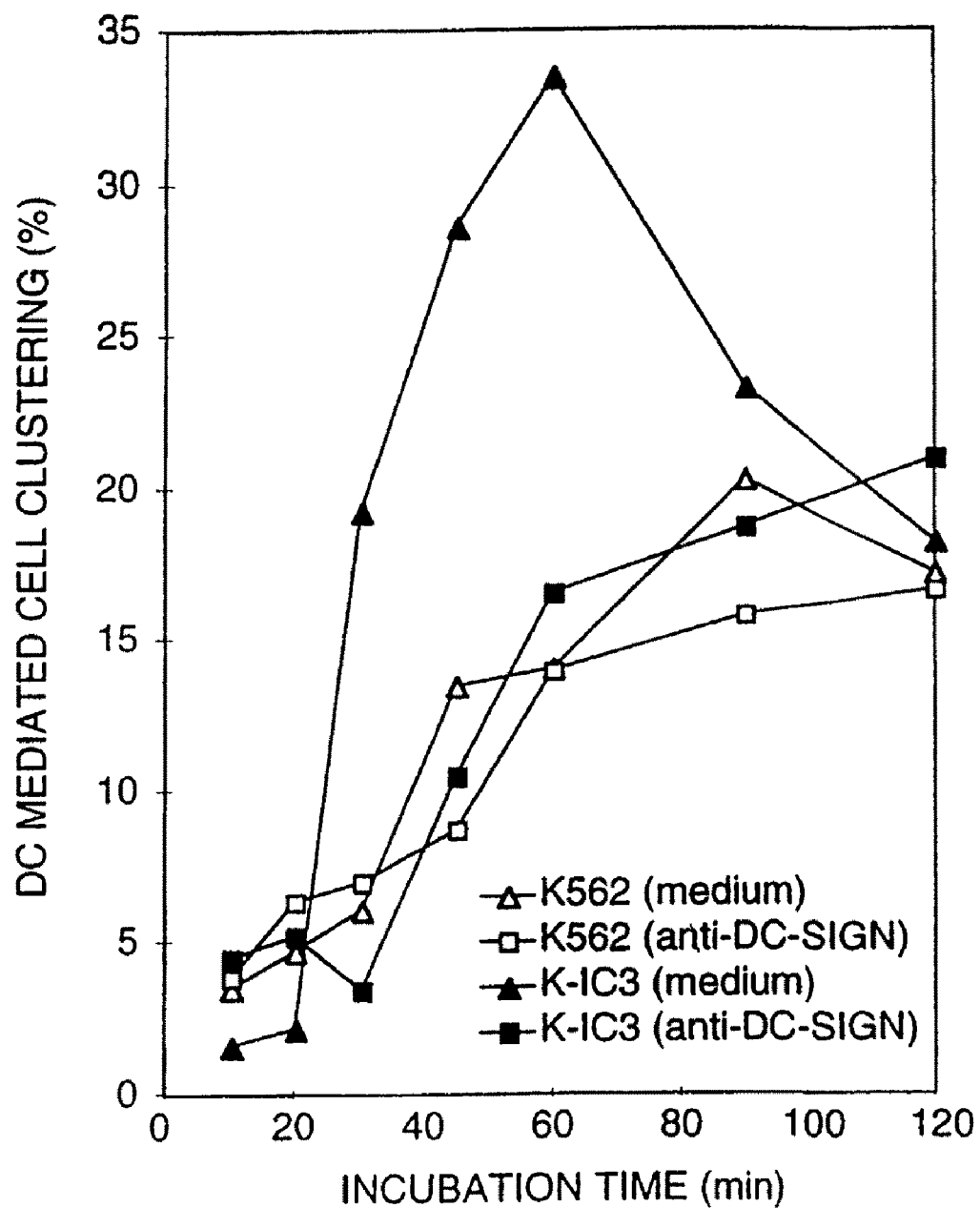

Fig 9

```
1/1                                    31/11
ATG AGT GAC TCC AAG GAA CCA AGA CTG CAG CAG CTG GGC CTC CTG GAG GAG GAA CAG CTG
Met ser asp ser lys glu pro arg leu gln gln leu gly leu leu glu glu glu gln leu
61/21                                  91/31
AGA GGC CTT GGA TTC CGA CAG ACT CGA GGA TAC AAG AGC TTA GCA GGG TGT CTT GGC CAT
arg gly leu gly phe arg gln thr arg gly tyr lys ser leu ala gly cys leu gly his
121/41                                 151/51
GGT CCC CTG GTG CTG CAA CTC CTC TCC TTC ACG CTC TTG GCT GGG CTC CTT GTC CAA GTG
gly pro leu val leu gln leu leu ser phe thr leu leu ala gly leu leu val gln val
181/61                                 211/71
TCC AAG GTC CCC AGC TCC ATA AGT CAG GAA CAA TCC AGG CAA GAC GCG ATC TAC CAG AAC
ser lys val pro ser ser ile ser gln glu gln ser arg gln asp ala ile tyr gln asn
241/81                                 271/91
CTG ACC CAG CTT AAA GCT GCA GTG GGT GAG CTC TCA GAG AAA TCC AAG CTG CAG GAG ATC
leu thr gln leu lys ala ala val gly glu leu ser glu lys ser lys leu gln glu ile
301/101                                331/111
TAC CAG GAG CTG ACC CAG CTG AAG GCT GCA GTG GGT GAG CTT CCA GAG AAA TCT AAG CTG
tyr gln glu leu thr gln leu lys ala ala val gly glu leu pro glu lys ser lys leu
361/121                                391/131
CAG GAG ATC TAC CAG GAG CTG ACC CGG CTG AAG GCT GCA GTG GGT GAG CTT CCA GAG AAA
gln glu ile tyr gln glu leu thr arg leu lys ala ala val gly glu leu pro glu lys
421/141                                451/151
TCT AAG CTG CAG GAG ATC TAC CAG GAG CTG ACC TGG CTG AAG GCT GCA GTG GGT GAG CTT
ser lys leu gln glu ile tyr gln glu leu thr trp leu lys ala ala val gly glu leu
481/161                                511/171
CCA GAG AAA TCT AAG ATG CAG GAG ATC TAC CAG GAG CTG ACT CGG CTG AAG GCT GCA GTG
pro glu lys ser lys met gln glu ile tyr gln glu leu thr arg leu lys ala ala val
541/181                                571/191
GGT GAG CTT CCA GAG AAA TCT AAG CAG CAG GAG ATC TAC CAG GAG CTG ACC CGG CTG AAG
gly glu leu pro glu lys ser lys gln gln glu ile tyr gln glu leu thr arg leu lys
601/201                                631/211
GCT GCA GTG GGT GAG CTT CCA GAG AAA TCT AAG CAG CAG GAG ATC TAC CAG GAG CTG ACC
ala ala val gly glu leu pro glu lys ser lys gln gln glu ile tyr gln glu leu thr
661/221                                691/231
CGG CTG AAG GCT GCA GTG GGT GAG CTT CCA GAG AAA TCT AAG CAG CAG GAG ATC TAC CAG
arg leu lys ala ala val gly glu leu pro glu lys ser lys gln gln glu ile tyr gln
721/241                                751/251
GAG CTG ACC CAG CTG AAG GCT GCA GTG GAA CGC CTG TGC CAC CCC TGT CCC TGG GAA TGG
glu leu thr gln leu lys ala ala val glu arg leu cys his pro cys pro trp glu trp
781/261                                811/271
ACA TTC TTC CAA GGA AAC TGT TAC TTC ATG TCT AAC TCC AGG CGG AAC TGG CAC GAC TCC
thr phe phe gln gly asn cys tyr phe met ser asn ser gln arg asn trp his asp ser
841/281                                871/291
ATC ACC GCC TGC AAA GAA GTG GGG GCC CAG CTC GTC GTA ATC AAA AGT GCT GAG GAG CAG
ile thr ala cys lys glu val gly ala gln leu val val ile lys ser ala glu glu gln
901/301                                931/311
AAC TTC CTA CAG CTG CAG TCT TCC AGA AGT AAC CGC TTC ACC TGG ATG GGA CTT TCA GAT
asn phe leu gln leu gln ser ser arg ser asn arg phe thr trp met gly leu ser asp
961/321                                991/331
CTA AAT CAG GAA GGC ACG TGG CAA TGG GTG GAC GGC TCA CCT CTG TTG CCC AGC TTC AAG
leu asn gln glu gly thr trp gln trp val asp gly ser pro leu leu pro ser phe lys
1021/341                               1051/351
CAG TAT TGG AAC AGA GGA GAG CCC AAC AAC GTT GGG GAG GAA GAC TGC GCG GAA TTT AGT
gln tyr trp asn arg gly glu pro asn asn val gly glu glu asp cys ala glu phe ser
1081/361                               1111/371
GGC AAT GGC TGG AAC GAC GAC AAA TGT AAT CTT GCC AAA TTC TGG ATC TGC AAA AAG TCC
gly asn gly trp asn asp asp lys cys asn leu ala lys phe trp ile cys lys lys ser
1141/381                               1171/391
GCA GCC TCC TGC TCC AGG GAT GAA GAA CAG TTT CTT TCT CCA GCC CCT GCC ACC CCA AAC
ala ala ser cys ser arg asp glu glu gln phe leu ser pro ala pro ala thr pro asn
1201/401
CCC CCT CCT GCG TAG
pro pro pro ala END
```

COMPOSITION AND METHOD FOR MODULATING DENDRITIC CELL-T CELL INTERACTION

This application is a continuation of U.S. application Ser. No. 10/625,204 filed Jul. 23, 2003, now U.S. Pat. No. 7,285,642, which is a divisional of U.S. application Ser. No. 09/719,961 filed 24 Sep. 2001, now U.S. Pat. No. 7,148,329, which is a U.S. National Stage filing of International Application No. PCT/NL00/00253 filed 19 Apr. 2000, which claims priority to EP Application No. 99201204.7 filed 19 Apr. 1999. International Application No. PCT/NL00/00253 further claims the benefit of U.S. Application No. 60/176,924 filed 20 Jan. 2000. All of the foregoing applications are hereby incorporated herein by reference in their entirety. The present invention relates to compositions and a method for modulating, in particular increasing or reducing, the immune response in an animal, such as a human or another mammal.

More specifically, this embodiment of the invention relates to compositions and a method for modulating, and in particular reducing, the adhesion of C-type lectin receptors on the surface of dendritic cells to the ICAM-receptors on the surface of T cells. By modulating this adhesion, both dendritic cell-T cell interactions, such as cluster formation and antigen presentation, as well as for instance primary T cell responses dependant thereon, can be influenced, resulting in a modulation of the immune response.

The compositions and method of the invention can therefore be used to alter immune responses to specific antigens as well as immune responses caused by disorders of the immune system, such as may occur in auto-immune diseases or in allergy.

In a further embodiment, the method of the invention can further be used in the treatment of HIV-infections and similar disorders of the immune system, as well as to modulate the immune response to grafts or after transplant.

In another embodiment, the invention relates to compounds, compositions and methods for modulating, and in particular increasing, the immune response in an animal, such as a human or another mammal.

More specifically, in this embodiment, an immune response against a specific antigen is generated, increased or promoted by presenting said antigen or an antigenic part thereof to dendritic cells in a form that can bind to the C-type lectin receptors on the surface of dendritic cells. The antigen presented in this manner enters the dendritic cell, which in turn presents the antigen to the T-cells, thereby causing an immune response, or an increased immune response, against the antigen.

Further embodiments of the invention relate to prophylactic techniques as well as diagnostic techniques using the compositions and/or embodying the methods as described above.

The invention is based on the surprising discovery that the adhesion of dendritic cells to T cells is mediated by a C-type lectin receptor on the surface of the dendritic cells. It has also been found that this C-type lectin binds to the ICAM receptors on the surface of T cells. With the term "ICAM receptor(s)" both the ICAM-2 and ICAM-3 receptor are meant, and in particular the ICAM-3 receptor.

The invention is further based on the finding that the inhibition of this C-type lectin receptor on the dendritic cells, such as by known inhibitors of C-type lectins and/or by specific antibodies directed against the C-type lectin receptor, can modulate, and more specifically reduce, the adhesion of T cells to dendritic cells, and can thereby influence the immune response, in particular the initial stages of the immune response.

WO 96/23882 describes a murine and human receptor with C-type lectins domains that is abundantly expressed on the surface of dendritic cells and thymic epithelial cells. The murine receptor—named "DEC-205"—is described as a 205 kDa protein with an isoelectric point of about 7,5 that contains 10 C-type lectin domains and that is homologous to the macrophage mannose receptor (MMR).

WO 96/23882 further describes monoclonal and polyclonal antibodies against DEC-205. However, these antibodies were not able to block dendritic cell function. In particular, monoclonal and polyclonal anti-DEC-205 antibodies were unable to inhibit the interaction between dendritic cells and helper T cells, both in vitro (as determined by the inability of anti-DEC-205 to inhibit allogenic T cell proliferation in a one way mixed leucocyte reaction) and in vivo (as determined by the inability of anti-DEC-205 to inhibit an in vivo response, i.e. in a local graft-versus-host (GVH) reaction). These results suggest that the DEC-205 receptor is not involved in dendritic cell-T cell interaction (i.e. adhesion) and that the anti-DEC-205 antibodies cannot be used to modulate the immune response.

Curtis et al., in *Proc. Natl. Acad. Sci.* USA, 89 (1992), p. 8356-8360, as well as in WO 93/01820, describe a non-CD4 gp120 receptor isolated and cloned from human placenta tissue. This gp120 receptor is expressed on mammalian cells which do not exhibit high levels of CD4, such as placenta, skeleton muscle, brain, neural and mucosal cells, as well as other tissues and cells including colon, thymus, heart, T cells, B cells and macrophages (but not in the liver or the kidney). The amino acid sequence of the C-type lectin gp120 receptor disclosed in SEQ ID NOs: 1 and 2 of WO 93/01820 is identical to the C-type lectins that are now found to be present on dendritic cells.

Curtis and WO 93/01820 further discuss the role this C-type lectin receptor plays in the infection of the aforementioned cells/tissues with HIV, i.e. by binding the major HIV envelope glycoprotein gp120 prior to internalization of the virion into the cell. It was found that inhibition of the C-type lectin gp120 receptor can reduce or inhibit HIV infection of these cells/tissues. As suitable inhibitors, WO 93/01820 discloses mannose carbohydrates, fucose carbohydrates, plant lectins such as concanavalin A, specific antibiotics such as pradimicin A, and sugars such as N-acetyl-D-glucosaminie and galactose (which however are described as less potent). These compounds and compositions containing them are used either in vitro or in vivo to inhibit the binding of HIV to the cell surface.

WO 93/01820 further discloses that binding of HIV to COS-7 cells can be inhibited by pre-incubation of gp120 with an anti-gp120 monoclonal antibody (named "antibody 110.1"). However, this antibody is not directed against the C-type lectins, but against the gp120 protein.

However, neither Curtis nor WO 93/01820 mentions or suggests the presence of such a C-type lectin on dendritic cells, nor do these references mention or suggest their role in dendritic cell—T cell interaction during the initial stages of an immune response.

WO 95/32734 describes FcγRII (CD32) bridging (or crosslinking) compositions and their use in modulating the immune response to specific antigens. This reference is based upon the finding that the bridging of FcγRII (CD32) molecules on antigen presenting cells (APCs) impaires the expression of the essential co-stimulatory molecules B7-1/2 (i.e. prevents their up-regulation) and causes thereby impaires the expression of (i.e. causes the down-modulation of) the adhesion molecule ICAM-3, with the functional consequence of an impaired capacity of the monocytes to co-stimulate the activation of antigen-specific T cells (i.e. resulting in the modulation of antigen-specific T cell unresponsiveness). The bridging agent is chosen from aggregrated human IgG molecules or Fc-fragments thereof; bi- or multivalent monoclonal antibodies to FcγRII or fragments thereof, or a fusion of two or more humane IgG Fc parts.

WO 95/32734 is therefore directed towards modulating (i.e. inhibiting) the co-stimulation signal required for T cell activation (i.e. besides the primary signal of TcR/CD3 interaction), in particular to induce proliferation and maturation into effector cells. WO 95/32734 is not directed towards modulating dendritic cell—T cell adhesion, nor does it disclose or suggest either the presence of C-type lectins on (the surface of) dendritic cells or their interaction with the ICAM-3 receptors on T cells.

WO 98/02456 discloses a group II human C-type lectin isolated from a stimulated human macrophage library. WO 98/49306 discloses a group IV C-type lectin present in human pancreatitis-associated protein ("PAP"). WO 98/41633 discloses a group V human C-type lectin isolated from a human tumor clone.

WO 98/02456, WO 98/49306 and WO 98/41633 further disclose methods for producing antibodies against these C-type lectins.

However, none of these references relates to C-type lectins on dendritic cells; the C-type lectins disclosed in these References differ from the C-type lectins described therein in origin, in biological function, and in structure.

Dendritic cells (DC) are professional antigen-presenting cells that capture antigens in the peripheral tissues and migrate via lymph or blood to the T cell area of draining lymph nodes and spleen. Here they present processed antigens to naive T cells, initiating antigen-specific primary T cell responses.

Due to their position in the body surface as immunosurveillance cells, it is likely that DC are the first cells infected with HIV-1 after mucosal exposure and are therefore implicated to play an important role in the immunopathogenesis of HIV. It is now generally believed that HIV converts the normal ticking process of DC to gain entry into lymph nodes and access to CD4$^+$ T cells, as was demonstrated in vivo using primary simian immunodeficiency virus infection of macaque as a model system (Spira et al., 1996)(Joag et al., 1997). Productive infection of DC with HIV-1 has been reported by several investigators (Granelli-Piperno et al., J Virol 72(4), 2733-7, 1998) (Blauvelt et al., Nat Med 3(12), 1369-75. 1997.) and substantial evidence indicates that DC pulsed with HIV-1 in vitro can induce a vigorous infection when co-cultured with T cells (Cameron et al., Science 257 (5068), 383-7, 1992). Although it is still unclear whether a similar scenario occurs in HIV infected individuals, HIV-1 transmission from DC to T cells could contribute to the CD4$^+$ T cell depletion observed in AIDS. Studying HIV-DC interactions should contribute to the understanding of early events of HIV infection and will hopefully lead to strategies aimed at blocking early events in transmission. For a further discussion, reference is also made to WO 95/32734 and WO 96/23882.

DC are unique in their ability to interact with and activate resting T cells. However, prior to the present invention, it was largely unknown how DC-T cell contact is initiated and regulated. Herein, the role of ICAM-3 in DC-T cell inter-actions is investigated. It is demonstrated that although DC strongly adhere to ICAM-3, this adhesion is not mediated by LFA-1, αD or any other integrin. In the search for this novel ICAM-3 receptor on DC a C-type lectin receptor was cloned, designated DC-SIGN, that is preferentially expressed by DC. Besides its prominent role in DC-T cell clustering and initiation of T cell responses we discovered that DC-SIGN is a major HIV-1 receptor involved in infection of DC and subsequent HIV-1 transmission to T cells. Thus HIV-1 and resting T cells exploit a similar highly expressed receptor to interact with DC.

In a first aspect, the invention relates to the use of a compound that binds or can bind to a C-type lectin on the surface of a dendritic cell, in the preparation of a composition for modulating, in particular reducing, the immune response in a animal, in particular a human or another mammal.

In particular, this aspect of the invention relates to the use of a compound that binds or can bind to a C-type lectin on the surface of a dendritic cell, in the preparation of a composition for modulating, in particular inhibiting, the interaction(s) between a dendritic cell and a T cell.

More in particular, this aspect of the invention relates to the use of a compound that binds or can bind to a C-type lectin on the surface of a dendritic cell in the preparation of a composition for modulating, in particular reducing, the adhesion between a dendritic cell and a T cell.

Especially, this aspect of the invention relates to the use of a compound that binds or can bind to a C-type lectin on the surface of a dendritic cell in the preparation of a composition for modulating, in particular reducing, the adhesion between a C-type lectin on the surface of a dendritic cell and an ICAM receptor on the surface of a T cell.

The amino acid sequence of one C-type lectin that was found to be involved in the binding of the dendritic cells to the T-cells is shown in SEQ ID NO: 2 and FIG. 9. This C-type lectin receptor is identical to the C-type lectin gp120 receptor described by Curtis et al, in *Proc. Natl. Acad. Sci.* USA, 89 (1992), p. 8356-8360 and the amino acid sequence given in SEQ ID NO: 1 of WO 93/01820. It is a group II C-type lectin of 404 amino acids; with an apparent Mr of about 44 kDa; and with a first domain (Met 1 to Ala 76) comprising a cytoplasmic amino terminus, a second domain (Ile 77 to Val 249) comprising tandem repeats, and a third domain (Cys 253 to Ala 404) with a high degree of homology to other known C-type lectins which are type II membrane proteins. Further characterisation is given below.

In the invention, this C-type lectin on dendritic cells was found to bind to ICAM receptors on the surface of T-cells.

Accordingly, the compositions of the invention can be used to modulate (i.e. alter and/or modify), and more specifically inhibit (i.e. reduce and/or down-tune), the interaction(s) between dendritic cells and T cells.

Such interactions include the adhesion of T-cells to dendritic cells, for instance in dendritic cell—T cell clustering, T-cell activation and further include all interactions that rely on contact between dendritic cells and T-cells, by which is meant either direct cell-to-cell contact or close proximity of dendritic cells and T cells.

Such further interactions includes but are not limited to, processes involved in generating an immune response, in particular during the initial stages of such a response, such as primary sensitation/activation of T-lymphocytes, (i.e. presentation of antigen and/or MHC-bound peptides to T-cells) and co-stimulation of T cells; as well as processes such as chemical signalling, endocytosis and transepithelial transport. For a discussion of dendritic cell-T cell interactions in general, all of which may be influenced by the compositions of the invention, reference is made to the discussion below as well as to WO 95/32734 and WO 96/23882.

The compositions of the invention can therefore be used to influence the immunomodulatory ability of dendritic cells; to modulate, and in particular reduce, dendritic cell-mediated (primary) T cell responses, and/or generally to influence, and in particular inhibit, the immune system.

Some specific applications include preventing or inhibiting immune responses to specific antigens; inducing tolerance; immunotherapy; immunosuppression, for instance to prevent transplant rejection; the treatment of auto-immune diseases such as thyroiditis, rheumatoid arthritis, systemic lupus erythematosus (SLE), multiple sclerosis and auto-immune diabetes; and the prevention or treatment of allergies.

The compositions of the invention may also modulate the activation of other receptors on T cells which are dependant upon the adhesion or close proximity of dendritic cells to T cells. Furthermore, the finding of the invention that a C-type lectin on dendritic cells binds to the ICAM receptors on T cells may open up new strategies or possibilities for influencing the interaction between dendritic cells and T cells, and thereby for modulating the immune system in general.

Furthermore, the compositions of the invention can be used to prevent or reduce the transfer of matter from dendritic cells to T cells, such as chemicals, signalling factors such as chemokines and/or interleukines, etc., and in particular of viral particles such as HIV. In this way, by using the compositions of the invention, not only can the initial adhesion of HIV to dendritic cells be inhibited, but also the spread of HIV infection from dendritic cells to T cells.

This finding is of particular importance as it is thought that dendritic cells may serve as a "reservoir" of HIV, in particular during the initial stages of HIV infection. The compositions of the invention can therefore not only be used to prevent HIV infection of dendritic cells, but also to reduce the spread of HIV infection to T cells after the dendritic cells have been infected, thereby slowing down the disease process.

Also, it is known that activation of T cells—i.e. in the lymph glands—plays an important role in the development of AIDS in a HIV-infected patient. It is believed that the compositions of the invention may be used to prevent, inhibit or at least delay said T-cell activation and thereby slow the onset and/or the progress of the disease.

Therefore, in a further aspect, the invention further relates to the use of a compound that binds or can bind to a C-type lectin on the surface of a dendritic cell, in the preparation of a composition for inhibiting the HIV infection of dendritic cells, in particular for inhibiting the adhesion of HIV surface protein (i.e. gp120) to the surface of a dendritic cell and thereby the entry of HIV into said dendritic cell.

The invention further relates to the use of a compound that binds or can bind to a C-type lectin on the surface of a dendritic cell, in the preparation of a composition for inhibiting the transfer of HIV from infected dendritic cells to non-infected T cells.

Compounds that can be used in the compositions of the invention include inhibitors for the C-type lectins known per se, including but not limited to those described in WO 93/01820 as mentioned above.

In general, these are compounds that can bind or adhere to (preferably in a reversible manner), or that can serve as a ligand for, the C-type lectins, in particular the C-type lectin of SEQ ID NO: 2/FIG. 9 or natural variants or equivalents thereof. Examples are mannose carbohydrates such as mannan and D-mannose; fucose carbohydrates such as L-fucose; plant lectins such as concanavalin A; antibiotics such as pradimicin A; sugars such as N-acetyl-D-glucosamine and galactose (which however are described as less potent); as well as suitable peptidomimetic compounds and small drug molecules, which can for instance be identified using phage display techniques. Furthermore, proteins such as gp120 and analogs or fragments thereof or similar proteins with binding capacity to C-type lectins on dendritic cells may be used, as well as isolated ICAM-receptors and analogs thereof, including part or fragments thereof. Such parts or fragments should then preferably still be such that they can bind to the C-type lectins on the surface of dendritic cells.

However, the use of carbohydrates is usually less desired from a therapeutic point of view, as such they can be rapidly metabolized in vivo. Also, the use of plant lectins such as concanavalin A and pradimicin antibiotics can have disadvantages in a therapeutic setting, in particular when treating patients with auto-immune disorders and/or HIV-infections.

Preferably, one or more physiological tolerable and/or pharmaceutically acceptable compounds are used, such as defined in WO 93/01820. For instance, the use of gp120 or derivatives thereof may cause undesired side effects, in particular on the nervous system (vide WO 93/01820).

Therefore, according to the invention, preferably an antibody directed against a C-type lectins as present/expressed on the surface of a dendritic cell, or a part, fragment or epitope thereof, is used. As used herein, the term antibodies includes inter alia polyclonal, monoclonal, chimeric and single chain antibodies, as well as fragments (Fab, Fv, Fa) and an Fab expression library. Furthermore, "humanized" antibodies may be used, for instance as described WO 98/49306.

Such antibodies against the C-type lectins of the invention can be obtained as described hereinbelow or in any other manner known per se, such as those described in WO 95/32734, WO 96/23882, WO 98/02456, WO 98/41633 and/or WO 98/49306.

For instance, polyclonal antibodies can be obtained by immunizing a suitable host such as a goat, rabbit, sheep, rat, pig or mouse with a C-type lectin or an immunogenic portion, fragment or fusion thereof, optionally with the use of an immunogenic carrier (such as bovine serum albumin or keyhole limpet hemocyanin) and/or an adjuvant such as Freund's, saponin, ISCOM's, aluminium hydroxide or a similar mineral gel, or keyhole limpet hemocyanin or a similar surface active substance. After an immuneresponse against the C-type lectins has been raised (usually within 1-7 days), the antibodies can be isolated from blood or serum taken from the immunized animal in a manner known per se, which optionally may involve a step of screening for an antibody with desired properties (i.e. specificity) using known immunoassay techniques, for which reference is againt made to for instance WO 96/23882.

Monoclonals may be produced using continuous cell lines in culture, including hybridoma and similar techniques, again essentially as described in the above cited references.

Fab-fragments such as F(ab)$_2$, Fab' and Fab fragments may be obtained by digestion of an antibody with pepsin or another protease, reducing disulfide-linkages and treatment with papain and a reducing agent, respectively. Fab-expression libraries may for instance be obtained by the method of Huse et al., 1989, Science 245:1275-1281.

Preferably, a monoclonal antibody against the C-type lectin(s) on dendritic cells is used, more specifically against the peptide with the amino acid sequence shown in/encoded for by SEQ ID no's 1 and 2 and FIG. 9, or (an antigenic) part thereof; and such monoclonals are a further aspect of the invention. Hereinbelow, the invention will be illustrated by means of two such monoclonals, herein referred to as AZN-D1 and AZN-D2, although similar monoclonals with comparable specificity for C-type lectins may also be used.

In a further aspect, the invention provides a cell line such as a hybridoma that produces antibodies, preferably monoclonal antibodies, against the C-type lectins on dendritic cells, more specifically against the peptide with the amino acid sequence shown in/encoded for by SEQ ID NOs. 1 and 2 and FIG. 9 or (an antigenic) part thereof. Hybridomas that produce the abovementioned monoclonals AZN-D1 and AZN-D2 of the invention were deposited on Apr. 8, 1999 with the European Collection of Cell Cultures, Porton Down, Salisbury, SP4 0JG, UK, under ECACC accession numbers 99040818 and 99040819, respectively.

The invention also relates to a method for producing an antibody, preferably a monoclonal antibody, against the C-type lectins on dendritic cells, more specifically against the peptide with the amino acid sequence shown in (or encoded for) by SEQ ID no's 1 and 2 and FIG. 9 or (an antigenic) part thereof, said method comprising cultivating a cell or a cell line that produces said antibody and harvesting/isolating the antibody from the cell culture.

Neither (monoclonal) antibodies against the C-type lectins on dendritic cells, nor cells or cell lines that produce such antibodies, have to date been described in the art, and it is envisaged that the novel antibodies of the invention will have broad applicability (i.e. besides the pharmaceutical/therapeutic uses disclosed herein). Some of these application—which form yet another aspect of the invention—will be clear to the skilled person from the disclosure herein.

For instance, the antibodies of the invention can be used to detect the presence of (and thereby determine the expression of) C-type lectins in or on tissues or whole cells, as well as the detect the presence of C-type lectins in other biological samples such as cell fragments or in cell preparations. The information thus obtained can then (also) be used to determine whether the method or compositions of the invention can be applied to such tissues or cells. The anti-bodies of the invention could also be used to detect (qualitatively and/or quantitatively), isolate, purify and/or produce dendritic cells, for instance in/from biological samples, including biological fluids such as blood, plasma or lymph fluid; tissue samples or cell samples such as bone marrow, skin tissue, tumor tissues, etc; or cell cultures or cultivating media.

For instance, the few methods presently available for isolating/producing dendritic cells from biological samples—such as the method described in U.S. Pat. No. 5,643,786, comprising leukapherese followed by fluorescence-activated cell-sorting—are very cumbersome multi-step procedures that provide only low yields and heterogenous samples. As a result, the limited availability of dendritic cells has severely hindered research into this important class of cells.

By using the monoclonals of the invention, dendritic cells could be isolated and produced with high(er) yield and with high specificity. In such a method, the monoclonals could be used in a manner known per se for the harvesting, isolation and/or purification of cells from biological fluids using antibodies.

For instance, the monoclonals could be attached to a column or matrix, to (para)magnetic beads or to a similar solid support, which could then be contacted with a biological sample or culture medium containing dendritic cells. The cells that do not attach themselves to the carrier are then separated or removed—e.g. by washing—after which the dendritic cells are separated from the carrier and isolated in a manner known per se.

Also, the monoclonals of the invention could be used to detect/determine the presence of dendritic cells (and/or C-type lectins) and/or the expression of genes coding therefor in biological samples, in which the antibodies could again be used in a manner known per se for the analytical of antibodies, such as competitive inhibition assays or ELISA-type immunoassays. For instance, the antibodies could be used in combination with microscopy techiques, cell sorting techniques including flow-cytometry and FACS, techniques based upon solid supports and/or detectable labels or markers (which can be attached to the antibodies), techniques baed upon (para) magenetic beads or any other detection or assay technique known per se in which antibodies can be used. Such assays and kits for therein—which besides the antibodies of the invention can contain all further components known per se for antibody-based assays, as well as manuals etc.—form a further aspect of the invention.

Thus, the monoclonals of the invention constitute a very useful diagnostic and research tool, for use both in vitro as well as in vivo. Possible non-limiting fields of application include the study of dendritic cells and their function and interactions; the study of the immune system; the detection of dendritic cells and/or C-type lectins in cells, tissues or biological fluids such as synovial tissue and skin tissue/skin cells (dermal dendritic cells); as well as the study of the role dendritic cells play in biological processes or disease mechanisms, such as cancer (as dendritic cells are exploited in vivo in clinical trials to eradicate tumor formation and development) and auto-immune diseases (including for instance rheumatoid arthritis).

For a further description of the methods and techniques known per se in which the antibodies of the invention can be used, reference is made to the general textbooks, such as D. P. Sites, A. I. Terr, T. G. Parslow: "Basic and clinical immunology", 8th Ed., Prentice-Hall (1994); I. Roitt, J. Brostof, D. Male: "Immunology", 2nd. Ed., Churchill Livingstone (1994); all incorporated herein by reference. Particular reference is made to the general uses of antibodies and techniques involved therein as mentioned in sections 2.7 to 2.17 of the general reference work by Janeway-Travers: "Immunobiology, the immune system in health and disease", Third Edition.

A composition of the invention may contain two or more of the above-mentioned active compounds, or such compounds may be used in combination. For instance, an anti-C-type lectin antibody can be formulated with mannose or fucose carbohydrates, lectins and/or antibiotics such as pridamicin A, whereby a synergistic effect may be obtained.

The compositions of the invention may also contain or be used in combination with known co-inhibitory compounds, such as anti-LF3A; as well as other active principles known per se, depending upon the condition to be treated. For instance, the compositions of the invention may be formulated or used in combination with immunosuppressants (i.e. for preventing transplant rejection), immunomodulants, antibiotics, auto-antigens or allergens (for instance as described in WO 95/3234 or WO 96/23882), Tumor Necrosis Factor (TNF), and anti-viral agents such as anti-HIV agents and CD4 inhibitors including CD4 directed antibodies such as Leu-3A, whereby again a synergistic effect can be obtained.

The compositions of the invention can further be formulated using known carriers and/or adjuvantia to provide a pharmaceutical form known per se, such as a tablet, capsule, powder, freeze dried preparation, solution for injection, etc., preferably in a unit dosage form. Such pharmaceutical forms, their use and administration (single or multi dosage form), as well as carriers, excipients, adjuvantia and/or formulants for use therein, are generally known in the art and are for instance described in WO 93/01820, WO 95/32734, WO 96/23882, WO 98/02456, WO98/41633 and/or WO 98/49306, all incorporated herein by reference. Furthermore, the formulation can be in the form of a liposome, as described in WO 93/01820.

Pharmaceutical formulations of antibodies, their administration and use, are generally described in WO 95/32734, WO 96/23882, WO 98/02456, WO 98/41633 and/or WO 98/49306

The compositions of the invention may further be packaged, for instance in vials, bottles, sachets, blisters, etc.; optionally with relevant patient information leaflets and/or instructions for use.

In a further aspect the invention relates to a method for modulating the immune response in an animal, in particular a human or another mammal, comprising administering to said animal a compound that binds or can bind to a C-type lectin on the surface of a dendritic cell, preferably in the form of a composition as described above, in an amount sufficient to alter or modify an immune response.

The compound or composition is in particular administered in such an amount that the interaction(s) between dendritic cells and T cells are altered or modified, more in particular in such an amount that the adhesion of dendritic cells to T cells is reduced.

This method can be used for preventing and/or treating disorders of the immune system, as well as to prevent transplant rejection, as described above.

The invention further relates to a method for the prevention or treatment of HIV infections, comprising administering to a HIV infected patient or a person at risk of becoming HIV infected, a compound that can binds or bind to a C-type lectin on the surface of a dendritic cell, in such an amount that the adhesion of HIV to the dendritic cells, and in particular of the gp120 envelop protein of HIV to the C-type lectin on the surface of dendritic cells, is inhibited.

Also, the invention further relates to a method for the treatment of HIV infections, comprising administering to a HIV infected patient a compound that binds or can bind to a C-type lectin on the surface of a dendritic cell, in such an amount that the transfer of HIV from infected dendritic cells to non-infected T cells is inhibited.

In a further aspect, the invention is used to modulate, and in particular generate, increase and/or promote, an immune response in an animal, such as a human or another mammal, against a specific antigen or combination of antigens, by presenting said antigen(s) or one or more antigenic parts thereof to dendritic cells in a form that can bind to the C-type lectin receptors on the surface of dendritic cells. The antigen(s) presented in this manner enter(s) the dendritic cell, which then in turn presents the antigen to the T-cells, thereby causing an immune response against the antigen(s).

With "a form that can bind to the C-type lectin receptors on the surface of dendritic cells" is generally meant that the antigen or antigenic fragment is attached to a compound, ligand or residu that can bind to a C-type lectin on the surface of a dendritic cell, such as the compounds/ligands mentioned above or a part thereof. Said attachment can for instance be by (preferably covalent) binding, ligand-ligand interaction, complexing, ligation, fusion of proteins (e.g. through expression of said fusions), or by any other type of physical or chemical interaction or bond that enables the antigen to be presented to a dendritic cell in conjunction with the ligand for the C-type lectin, i.e. combined into a stable or semi-stable entity.

For instance, the antigen can be provided with the above-mentioned mannose and fucose carbohydrates as covalently bound groups or side-chains; can be covalently attached to plant lectins such as concanavalin A or antibiotics such as pradimicin A; or can be provided with sugar residues such as N-acetyl-D-glucosamine and galactose (which however is less preferred), all of which serve to "direct" the antigen to the dendritic cell.

Preferably, the antigen is attached to (e.g. fused with or covalently bonded to) to a protein that can bind to or serve as a ligand for the C-type lectins, such as gp120 and analogs thereof or the ICAM-receptors and analogs thereof, or to a part of fragment of such a protein. Alternatively, the antigen can be attached to (e.g. fused with or covalently bonded to) an antibody directed against the C-type lectins, preferably a monoclonal antibody such as AZN-D1 and AZN-D2 mentioned above; or to a part or fragment of such an antibody as described above.

The antigen can be any antigen against which an (increased) immune response is to be obtained, or any part or fragment thereof. Preferably, any such part or fragment is such that it per se is capable of eliciting an immune response, such as an epitope. However, this is not required: because according to the invention the fragments are directed to the dendritic cells, i.e. with increased specificity or affinity, a part or fragment that would normally be incapable of eliciting an immune response may provide an immune response when used in conjunction with a ligand for the C-type lectins as described herein. Also, in general, using an antigen in combination with a ligand for the C-type lectins may increase the potency of the antigen, i.e. provide a higher or stronger immune response per unit of antigen administered. In this way, antigens—including those present in serums or vaccines, but also retroviral vectors encoding a desired antigen—could be administered at a lower dosage and still provide sufficient immune response.

Examples of suitable antigens are cancer antigens including gp 100, g250, p53, MAGE, BAGE, GAGE, MART 1, Tyrosinase related protein II and Tyrosinase related protein; all of which can be used to generate an immune response against the tumor cells that contain or express said antigen. Other types of antigen that can be used in the invention include essentially all antigens used in vaccines against (infectious) diseases, such as influenza, mumps, measles, rubella, diphteria, tetanus, diseases due to infection with micro-organisms such as *Haemophilus influenzae* (e.g. type b), *Neisseria, Bordetella pertussis, Polyomyletus,* Influenza virus and Pneumococcus, and generally any other infection or disease against which a vaccine can be developed or can be envisaged, including also parasitical, protozoan and/or viral infections such as HIV and herpes. To provide serums or vaccines, the compounds of the invention may further be combined with other antigens known per se.

This aspect of the invention therefore relates to the use of a combination of: 1) a compound that binds to a C-type lectin on the surface of a dendritic cell; and attached thereto: 2) an antigen or a fragment or part thereof; in the preparation of a composition for modulating, in particular generating, increasing and/or promoting, an immune response in a animal, in particular a human or another mammal, against said antigen.

These combinations (e.g. in the form of a complex, a chemical substance or entity, or a fused protein or protein structure), which as such form another aspect of the invention, can again be formulated and administered in a manner known per se, such as described above.

In all the above methods en embodiments, the compounds/compositions used will be administered in a therapeutically effective amount, for which term reference is generally made to WO 93/01820, WO 95/32734 and/or WO 96/23882. The administration can be a single dose, but is preferably part of a multidose administration regimen carried out over one or more days, weeks or months.

All terms used herein have the normal meaning in the art, for which reference can be made to inter alia the definitions given in WO 93/01820, WO 95/32734, WO 96/23882, WO 98/02456, WO98/41633 and/or WO 98/49306, analogously applied.

Furthermore, although the invention is described herein with respect to the specific 44 kDa C-type lectin receptor disclosed herein, it is not excluded that other, generally similar C-type lectins, including natural variants of the sequence of SEQ ID NO: 2 and FIG. 9, may also be present on dendritic cells and/or may be involved in dendritic cell—T cell interaction. Such variants will usually have a high degree of amino acid homology (more than 80% to more than 90%) with, and/or be functionally equivalent to the specific C-type lectin disclosed herein. Also, any such receptor will generally display properties similar to those as described herein; in particular that inhibition of this receptor, either by carbohydrate inhibitors or specific antibodies, will lead to an alteration of dendritic cell/T-cell interaction. Any such variant receptors should however be distinguished from the C-type lectin receptor disclosed in WO 96/23882, inhibition of which does not result in inhibition of the interaction of dendritic cells and T-cells.

The invention will now be further illustrated by means of the Experimental Part given hereinbelow, as well as the Figures, in which:

FIGS. 1A-1C are graphs showing: spontaneous adhesion of leukocytes to ICAM-1 and ICAM-3 (FIG. 1A); adhesion of leukocytes to ICAM-3 after activation of β2-integrins (FIG. 1B); adhesion of DC to ICAM-3 in the presence of blocking antibodies (20 μg/ml) against β2-integrins (NKI-L19), β1-integrin (AIIB2), ICAM-3 (CBR-IC3/1, CBR-IC3/2) or in the presence of EDTA (5 mM) or EGTA (5 mM) (FIG. 1C).

FIGS. 2A-2D are graphs showing that the antibodies AZN-D1 and AZN-D2 inhibit adhesion of DC to ICAM-3 and recognize an antigen that is specifically expressed by DC.

FIGS. 3A and 3B show that DC-SIGN is identical to human placenta HIV gp120 binding C-type lectin, as can be seen from SDS-PAGE (FIG. 3A) and by schematic presentation of DC-SIGN isolated from human DC (3B).

FIGS. 5A-D show the tissue distribution of DC-SIGN as determined by immunohistochemical analysis of the expression of DC-SIGN in tonsils (A and B) and lymph node sections (C and D) (OMx100).

Figure 6A:
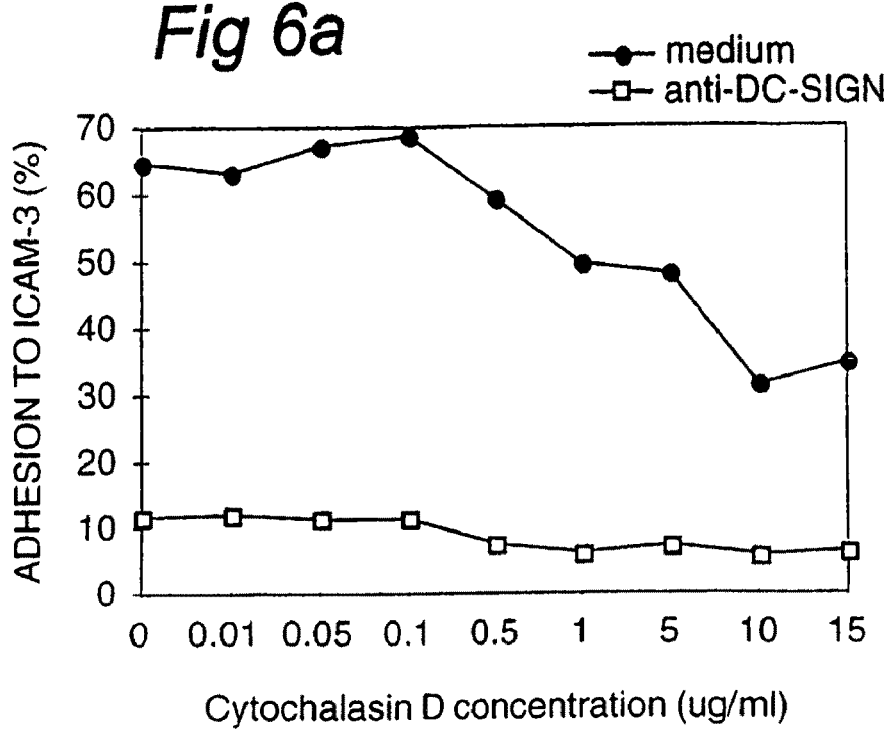
Figure 6C:
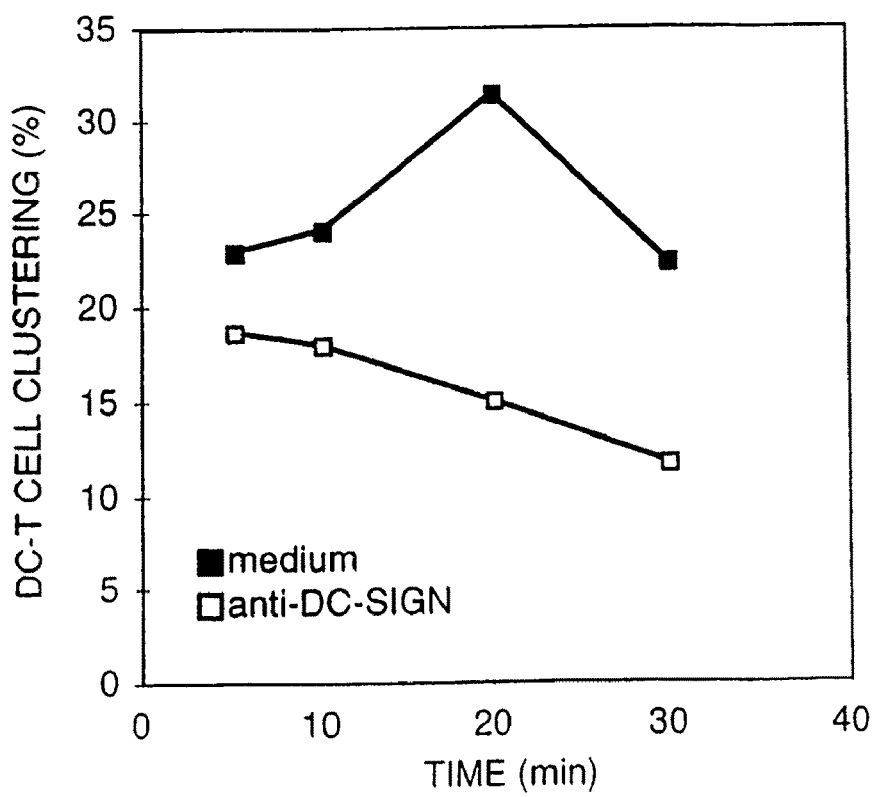
Figure 6D:
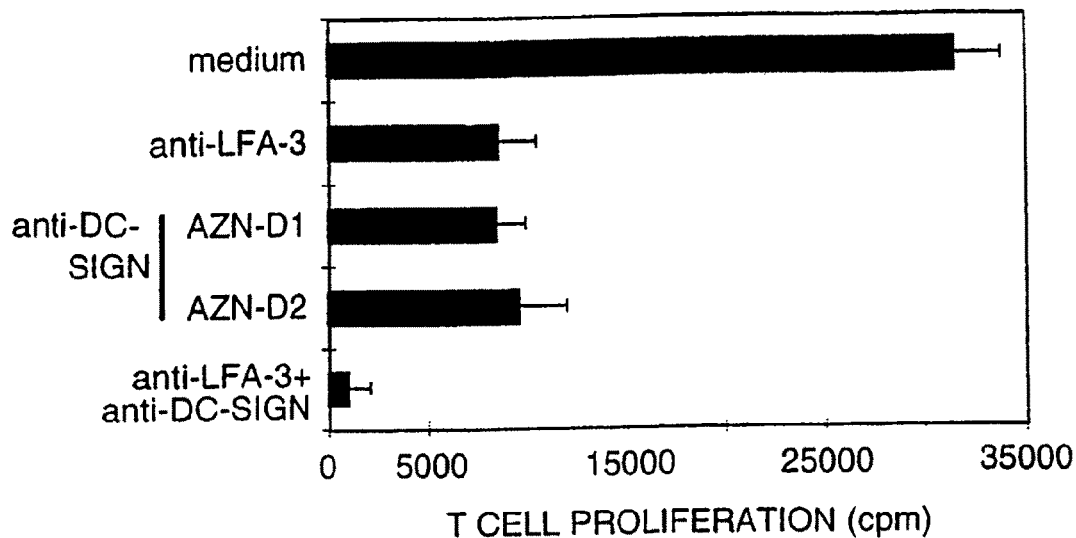

FIGS. 6A-6D show that DC-SIGN mediated adhesion of DC to ICAM-3 is involved in the DC-T-lymphocyte interaction, as demonstrated by DC-SIGN mediated adhesion of DC to ICAM-3 (FIG. 6A); heterotypic cell clustering of DC with K562-ICAM-3 cells (FIG. 6B); dynamic cell clustering of DC with resting PBL (FIG. 6C); and the role of DC-SIGN-ICAM-3 interaction plays in DC-induced T-cell proliferation (FIG. 6D).

Figure 7:
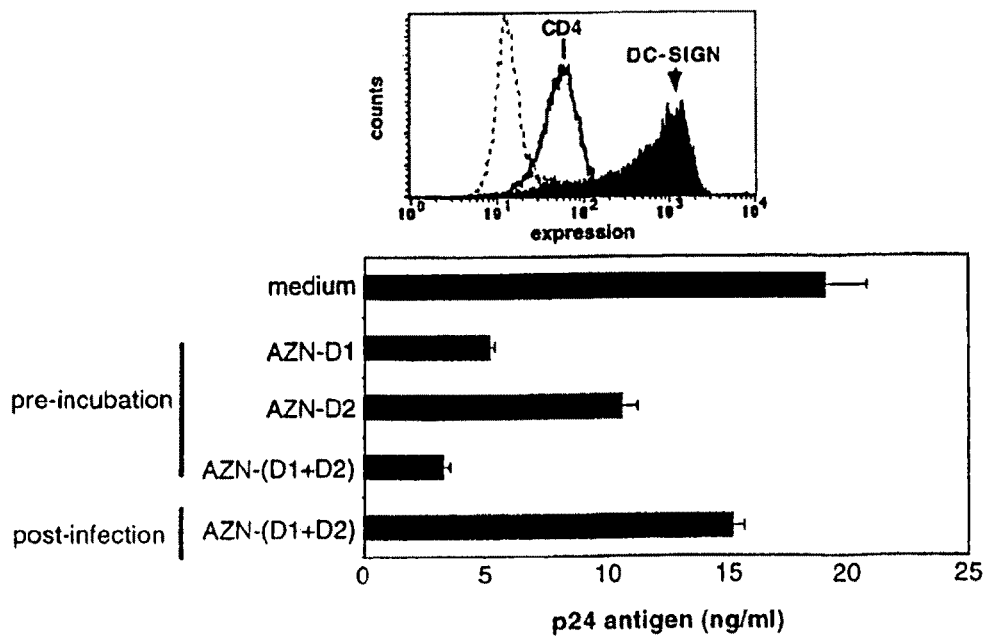

FIG. 7 shows that DC SIGN is a receptor for HIV-1 on DC.

Figure 8:
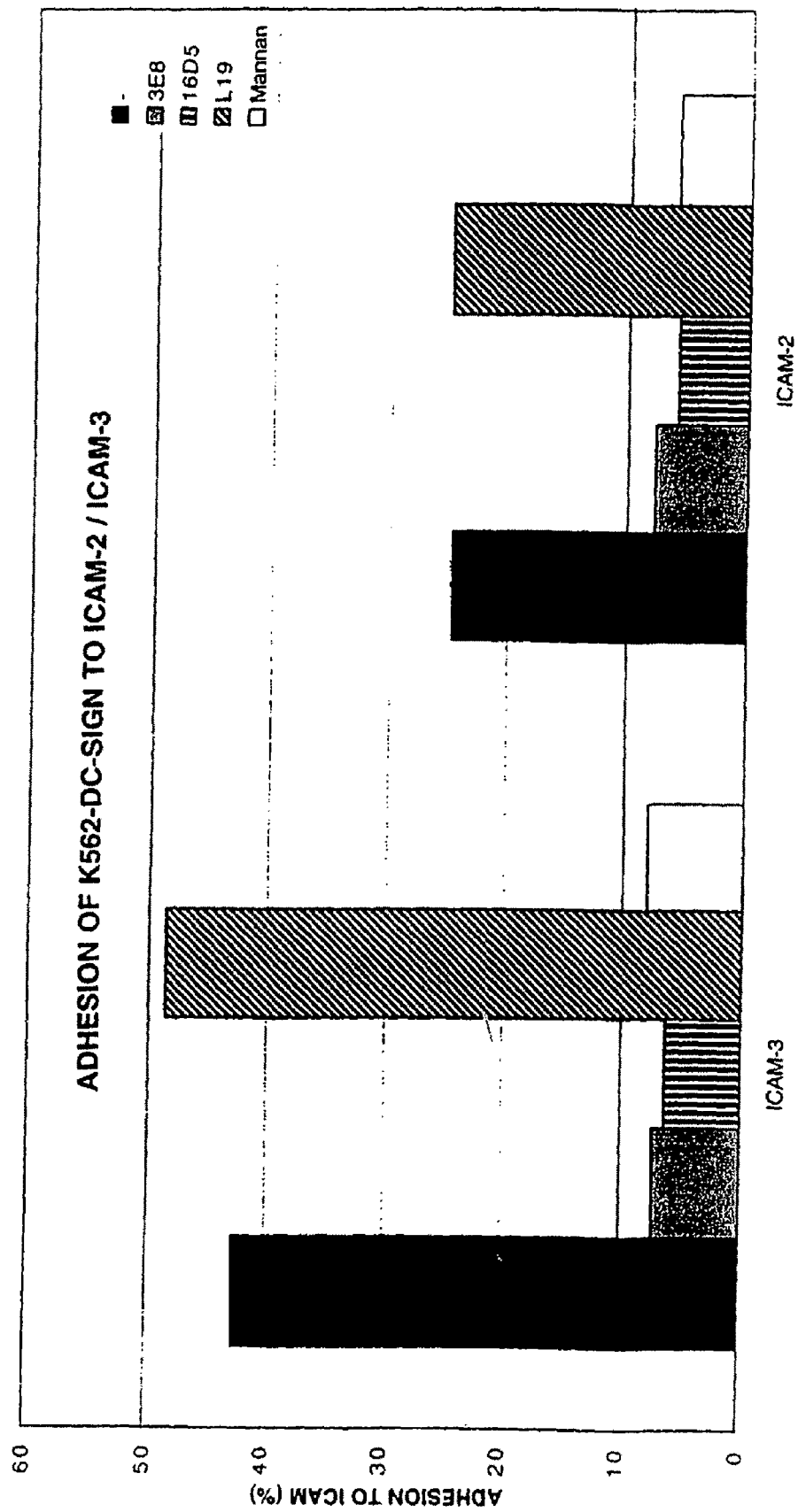

FIG. 8 shows that DC SIGN binds to both ICAM-2 as well as ICAM-3 expressing K562 cells.

FIG. 9 shows the sequence of DC-SIGN.

EXPERIMENTAL

Dendritic cells (DC) capture antigens and migrate to secondary lymphoid tissues where they present antigens to naive T cells. HIV-1 subverts this unique capacity to gain access to CD4$^+$ T cells. In the invention, a DC specific C-type lectin was cloned, designated DC-SIGN, that not only binds to ICAM-2 and/or ICAM-3 with high affinity but is also able to bind HIV-1. Also, anti-DC-SIGN antibodies were developed that not only inhibit transient DC-T cell interactions and DC induced T cell proliferation but also effectively inhibit HIV-1 infection of DC. These findings not only have important consequences for the understanding on CD4-independent HIV entry into DC but also shed new light on the role of DC-SIGN in initiating primary immune responses.

Example 1

Adhesion of DC to ICAM-3 is Not Mediated by Integrins

Figure 1A:
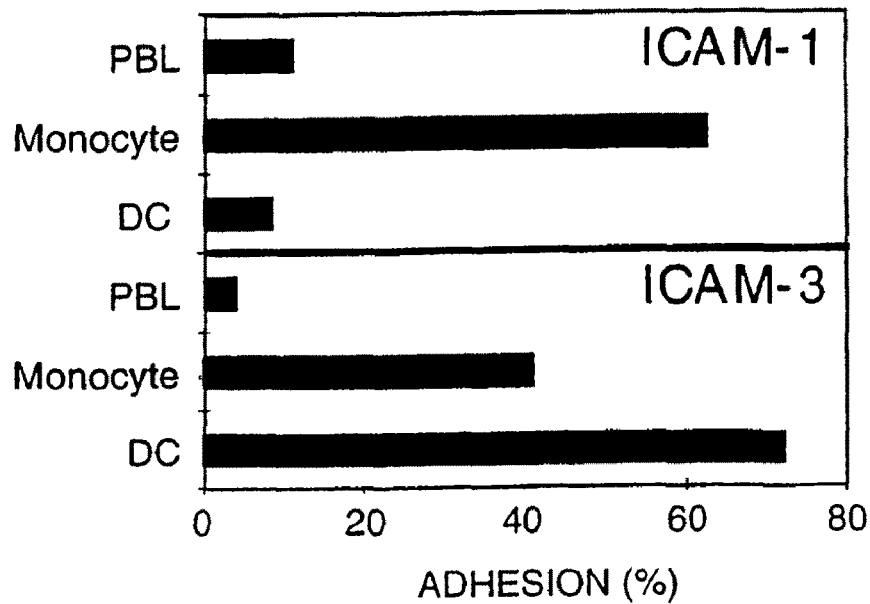

The role of ICAM-3 mediated adhesion in first DC-T cell contact was investigated. Exploiting a novel flowcytometric adhesion assay involving ICAM-3-Fc chimera coated fluorescent beads (Geijtenbeek et al.), the capacity of DC, resting peripheral blood lymphocytes (PBL) and monocytes to bind to this integrin ligand was tested. Immature DC, obtained after culturing of monocytes for 7 days in the presence of IL-4 and GM-CSF, strongly bind ICAM-3 without prior activation of β2 integrins (72%, FIG. 1A). FIG. 1 demonstrates that the adhesion of DC to ICAM-3 is $Ca^{2+}$-dependent and integrin-independent: in FIGS. 1A, B and C one representative experiment of at least 3 is shown (SD<5%).

1A: Spontaneous adhesion of leukocytes to ICAM-1 and ICAM-3. Freshly isolated PBL, monocytes and DC were incubated for 30 min. at 37° C. with either ICAM-1Fc or ICAM-3Fc fluorescent beads. After washing, the percentage of cells that bound beads was determined by flowcytometry.

1B: Adhesion of leukocytes to ICAM-3 after activation of β2-integrins. Binding of fluorescent ICAM-3Fc beads was measured after 30 min. at 37° C. in the presence of either PMA 980 nM) or the activating anti-β2-integrin antibody KIM185 (10 μg/ml). Inhibition of the LFA-1 specific adhesion after PMA activation was determined in the presence of the blocking anti-LFA-1 antibody NKI-L15 (20 μg/ml).

1C: Adhesion of DC to ICAM-3 in the presence of blocking antibodies (20 μg/ml) against β2-integrins (NKI-L19), β1-integrin (AIIB2), ICAM-3 (CBR-IC3/1, CBR-IC3/2) or in the presence of EDTA (5 mM) or EGTA (5 mM).

The adhesion was determined as described in FIG. 1A. This spontaneous binding of DC to ICAM-3 is stronger than that of monocytes, whereas resting PBL hardly bind ICAM-3 (FIG. 1A). Adhesion of DC to ICAM-3 could not be blocked with any anti-αL or anti-β2 integrin antibody (FIG. 1A). In contrast, adhesion of monocytes to ICAM-3 is LFA-1 dependent, since adhesion is blocked by anti-αL antibodies (FIG. 1A). Since neither antibodies directed against the other β2 integrin members (αDβ2, αMβ2, αXβ2, data not shown), nor antibodies directed against other integrins (β1, β7 integrins, FIG. 1B), blocked the adhesion of DC to ICAM-3, it was concluded that the binding of DC to ICAM-3 is integrin-independent.

Figure 1B:
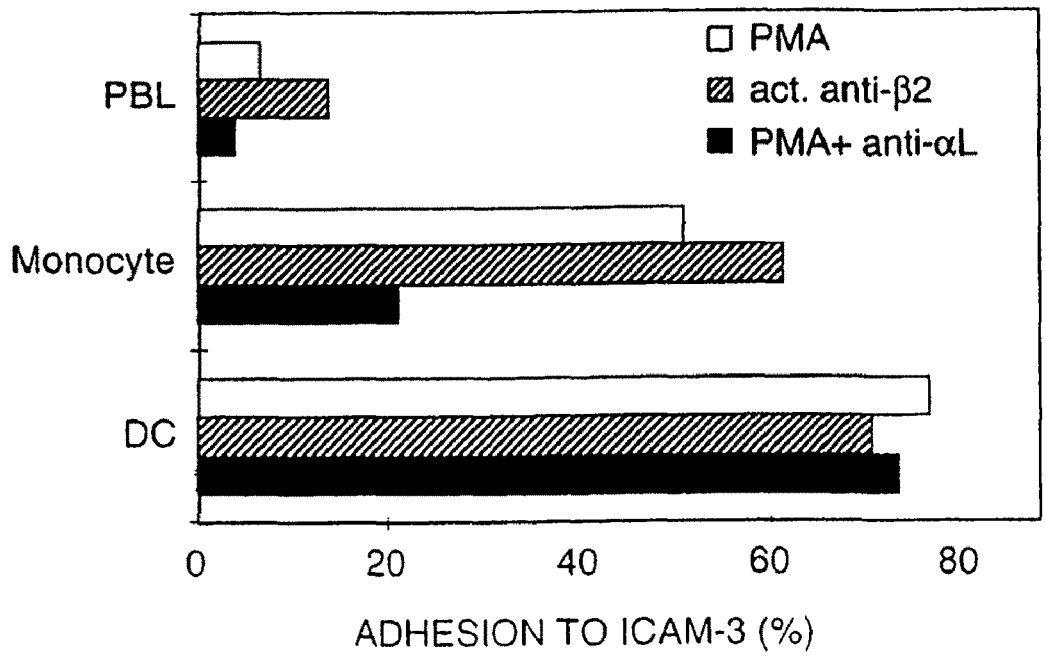

The interaction of DC with ICAM-3-Fc beads is ICAM-3 specific since the anti-ICAM-3 antibodies CBR3/1, CBR3/2 of the invention and a combination of both antibodies are able to inhibit the adhesion to a large extent (FIG. 1B). Interestingly, adhesion of DC to ICAM-3 could be completely blocked by EDTA and EGTA (FIG. 1B). These findings strongly suggest that DC bind ICAM-3 through a $Ca^{2+}$ dependent surface receptor that does not belong to the β1 or β2 integrin family. This molecule was designated: DC-Specific ICAM-3 Grabbing Non-integrin (DC-SIGN).

Example 2

Antibodies Against DC-SIGN Inhibit the DC-ICAM-3 Interaction

Figure 2A:
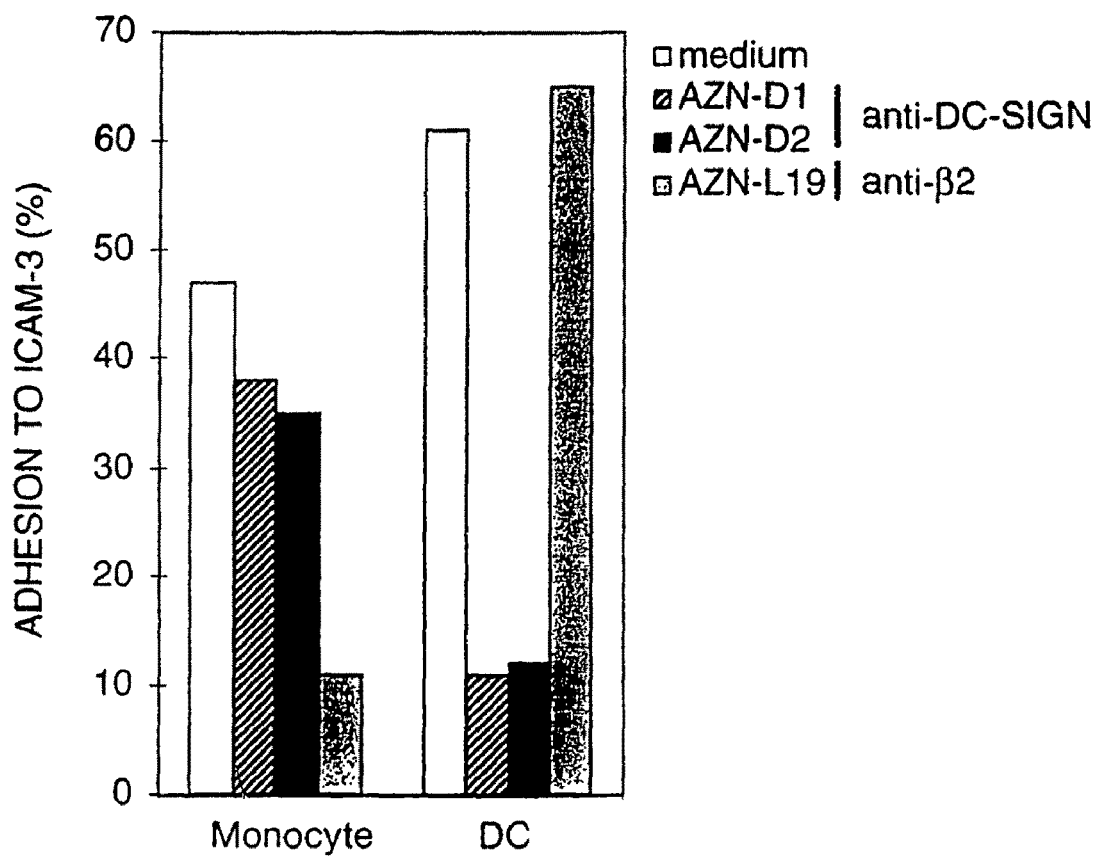
Figure 2D:
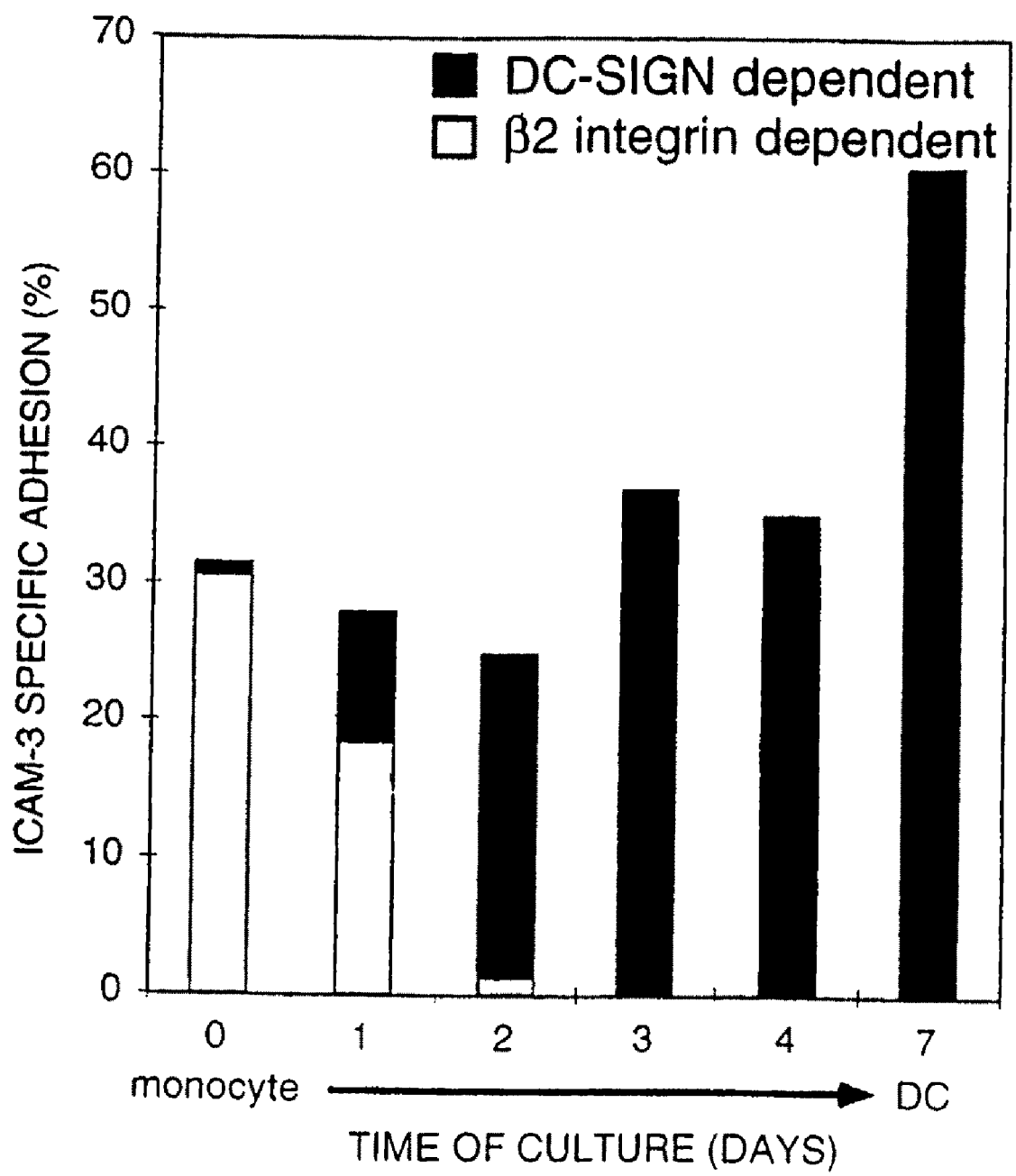

To investigate DC-SIGN in more detail, antibodies against the ICAM-3 binding receptor were raised. Spleens of mice immunized with DC were fused with SP2/0 myeloma cells and supernatants of the resulting hybridomas were screened for the presence of antibodies capable of inhibiting DC specific adhesion to ICAM-3. Two hybridomas were selected, cloned and the resulting antibodies were named AZN-D1 and AZN-D2. Both purified antibodies strongly inhibit adhesion of DC to ICAM-3, but do not affect LFA-1 mediated adhesion of monocytes to ICAM-3 (FIG. 2A). FIG. 2 demonstrates that antibodies AZN-D1 and AZN-D2 inhibit adhesion of DC to ICAM-3 and recognize an antigen that is specifically expressed by DC:
- 2A: The monoclonal antibodies AZN-D1 and AZN-D2 (20 μg/ml) block adhesion of DC but not that of freshly isolated monocytes to fluorescent ICAM-3Fc beads. A representative experiment of at least 3 experiments is shown (SD<5%).
- 2B: DC-SIGN expression increased during DC development. DC were cultured from monocytes in the presence of GM-CSF and IL-4. At different timepoints the developing DC were analyzed for expression of the monocyte marker CD14, β2 integrin LFA-1 and DC-SIGN. Cells were gated on forward-side scatter and the mean fluorescence is shown in the top right corner of the histograms. A representative experiment out of 3 is shown.
- 2C: DC developing from monocytes, in the presence of GM-CSF and IL4, increasingly bind to ICAM-3 in a DC-SIGN dependent manner. At different time points during culturing cells were harvested and incubated with fluorescent ICAM-3Fc beads in the presence of the blocking anti-β2-integrin antibody AZN-L19 or the AZN-D1 antibody (20 μg/ml). Adhesion was determined as described in FIG. 1A. AZN-D2 inhibited adhesion to ICAM-3 similar to AZN-D1 (results not shown). A representative experiment out of 3 is shown (SD<5%).
- 2D: Relative contribution of β2-integrins and DC-SIGN mediated adhesion to ICAM-3 by developing DC. Relative contribution is calculated from the inhibition of adhesion in the presence of AZN-D1 or AZN-L19 as described in FIG. 2C.

Using AZN-D1 antibodies in flowcytometric analyses it was demonstrated that DC-SIGN is not expressed by monocytes (FIG. 2B). Cells expressing DC-SIGN can already be detected after 1 day of culture. The expression level of DC-SIGN increases during culture (FIG. 2B). The expression of the monocyte marker CD14 gradually decreases during culture and at day 7 only a low CD14 expression is observed (FIG. 2B). Further flowcytometric analyses demonstrated that at day 7 the cells also express high levels of MHC Class I, II, the β2 integrin p150,95 and CD86 (data not shown), consistent with the differentiation of monocytes into immature DC. These results demonstrate that DC-SIGN is abundantly expressed by DC at day 7, the expression level is several fold higher than that of LFA-1.

Simultaneously, the involvement of DC-SIGN in ICAM-3 binding during the differentiation of monocytes into immature DC was investigated (FIG. 2C). At onset of the culture (day 0) binding to ICAM-3 by monocytes is completely β2 integrin (LFA-1) dependent, as demonstrated by inhibition of adhesion with the blocking anti-β2 integrin antibody L19 (FIG. 2C). At day 1, when low levels of DC-SIGN are expressed (FIG. 2B), ICAM-3 specific adhesion depends on both β2 integrin (LFA-1) and DC-SIGN (FIG. 2C). From day 2 to day 7 the ICAM-3-specific adhesion increases, becomes β2 integrin-independent (FIG. 2C) and from day 2 is solely mediated by DC-SIGN, since anti-DC-SIGN block the adhesion completely. Maximum adhesion through DC-SIGN is reached at day 7 (FIG. 2C).

Together these results demonstrate that the increase in expression of DC-SIGN coincides with the observed increase in ICAM-3 binding (FIGS. 2A and B). From these findings it can be concluded that DC-SIGN, recognized by the antibodies AZN-D1 and AZN-D2, is the novel ICAM-3 binding receptor expressed by DC.

Example 3

DC-SIGN is a 44 kDa Protein

To obtain information regarding the molecular weight of DC-SIGN DC-SIGN was immunoprecipitated from a lysate of $^{125}$I-surface labeled DC. Analysis by SDS-PAGE under reducing conditions revealed a single protein of 44 kDa (FIG. 3A, lanes 1-2). FIG. 3 demonstrates that DC-SIGN is identical to human placenta HIV gp120 binding C-type lectin:
- 3A: DC-SIGN is a 44 kDa protein DC were surface labeled with $I^{125}$, lysed and DC-SIGN was immunoprecipitated with the anti-DC-SIGN antibodies AZN-D1 (lane 1), AZN-D2 (lane 2) and AZN-L19 (anti-β2-integrin; lane 3). The immunoprecipitates were analyzed by SDS-PAGE (5-15% gel) followed by autoradiography. The migration of the molecular weight markers is indicated on the left. The arrows indicate the α-chains of LFA-1 (αL, 180 kDa), MAC-1 (αM, 165 kDa) and p150,95 (αX, 150 kDa), the β2 integrin chain (95 kDa) and DC-SIGN (44 kDa). Similar results were obtained in 3 other experiments.
- 3B: Schematic presentation of DC-SIGN isolated from human DC. The two boxed peptides (aminoacid positions 296-306 and 187-197 of the human placenta gp120 binding C-type lectin ( ) were identified by internal peptide sequencing of immunoprecipitated DC-SIGn using Edman degradation. The cDNA encoding DC-SIGN was isolated from DC. The deduced amino acid sequence is 100% identical to that of the human placenta gp120 binding C-type lectin ( ). The transmembrane region, the lectin domain and the seven complete and eight partial repeats (R1-R8) are indicated.

Analysis of the immunoprecipitate on a non-reducing SDS-PAGE gel shows that DC-SIGN exists as a monomer (results not shown). Furthermore, using ICAM-3-Fc coated beads also a 44 kDa protein could be extracted from the DC lysate whereas in the presence of blocking anti-DC-SIGN antibodies this protein could not be precipitated with ICAM-3-Fc coated beads (results not shown). These findings demonstrate that DC-SIGN is expressed by DC as a 44 kDa protein under reducing conditions. The observation that ICAM-3 Fc coupled beads only extracted a 44 kDa protein out of the DC lysate indicates that DC-SIGN has a high affinity for ICAM-3, much higher an LFA-1 or αDβ2 which are also expressed by DC (FIG. 3A) and have been reported to bind ICAM-3 (VanderVieren et al., Immunity. 3, 683-690, 1995). Since very low amounts of LFA-1 are immunoprecipitated in comparison to DC-SIGN (FIG. 3A, lane 1 and 3) this confirms that DC-SIGN is more abundantly expressed by DC than LFA-1. Together, these data demonstrates that DC-SIGN is a single polypeptide of 44 kDa and is the primary receptor for ICAM-3 on DC.

Example 4

DC-SIGN is Identical to the Human HIV gp120 Binding C-Type Lectin

To identify DC-SIGN, a preparative immunoprecipitation from a DC lysate with the anti-DC-SIGN antibody AZN-D1 was performed and the 44 kDa protein from the SDS-PAGE gel was excised. After tryptic digestion, the resulting peptides were extracted from the gel and purified using preparative HPLC. Subsequently, the amino acid sequences of 2 peptides (0.5-1 pmol) were determined using the Edman degradation procedure. Both peptides consisted of 11 amino acid residues (FIG. 3B; SEQ ID NOs:5 and 6) and the peptide sequences were used to screen the EMBL database for homology with known proteins. Both peptides proved 100% identical to the deduced amino acid sequence of the human HIV gp120-binding C-type lectin (Curtis et al., 1992). This protein has previously been identified exclusively in placenta as a CD4-independent receptor for the human immunodeficiency virus (HIV) envelope glycoprotein gp120.

Figure 3B:
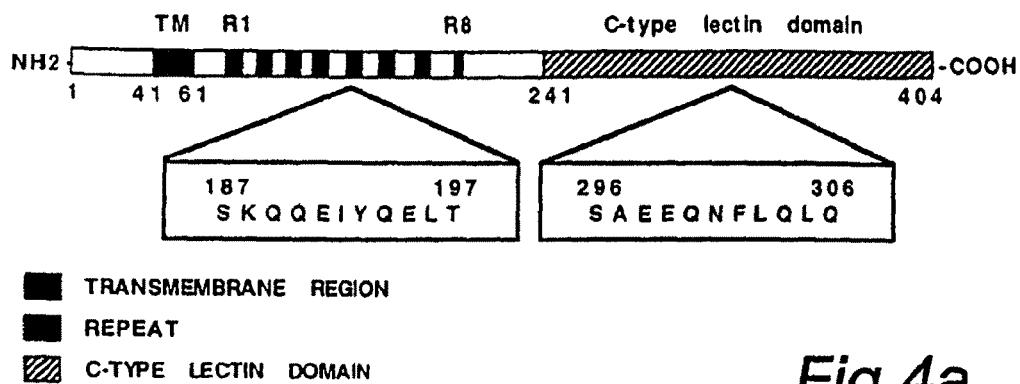
Figure 4A:
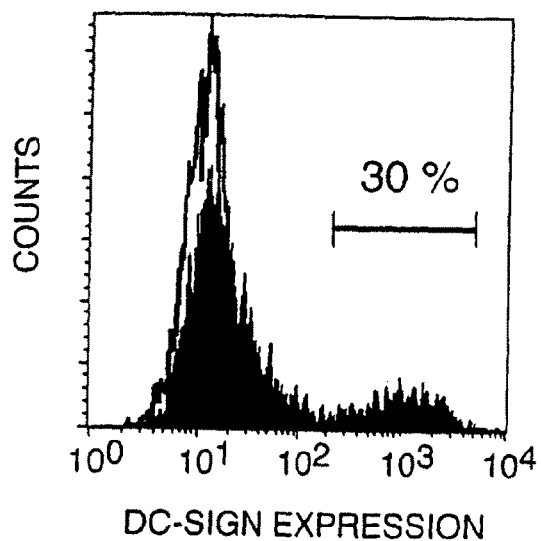
FIGS. 4A and 4B show that DC-SIGN, overexpressed in COS7 cells, is recognized by the anti-DC-SIGN antibody AZN-D1 and binds to ICAM-3.

RT-PCR analysis with primers based on the gp120-binding C-type lectin sequence, on RNA isolated from DC yielded a PCR product of the expected length of 1237 nt. The DC-specific PCR product was cloned and sequencing confirmed 100% identity with the human gp120-binding lectin (FIG. 3B). Flowcytometric analysis of COS7 cells, transfected with the cDNA encoding the placenta gp120-binding C-type lectin, unequivocally proves that the gp120 binding C-type lectin is indeed identical to DC-SIGN (FIG. 4A). FIG. 4 demonstrates that DC-SIGN, overexpressed in COS7 cells, is recognized by the anti-DC-SIGN antibody AZN-D1 and binds ICAM-3:

4A: AZN-D1 recognizes COS7 cells transfected with the cDNA encoding DC-SIGN (filled) and not mock transfected COS7 cells (open). AZN-D2 gave a similar staining (results not shown).

4B: Adhesion of COS7-DC-SIGN to ICAM-3. COS7 cells were transfected and the adhesion was determined as described in FIG. 1A, respectively. Adhesion of COS7-DC-SIGN cells to ICAM-3 was measured in the presence of EGTA (5 mM) and blocking antibodies against DC-SIGN (AZN-D1), ICAM-3 (CBR-IC3/1, CBR-IC3/2) and β2 integrinds (AZN-L19). A representative experiment out of 3 is shown (SD<5%).

Figure 4B:
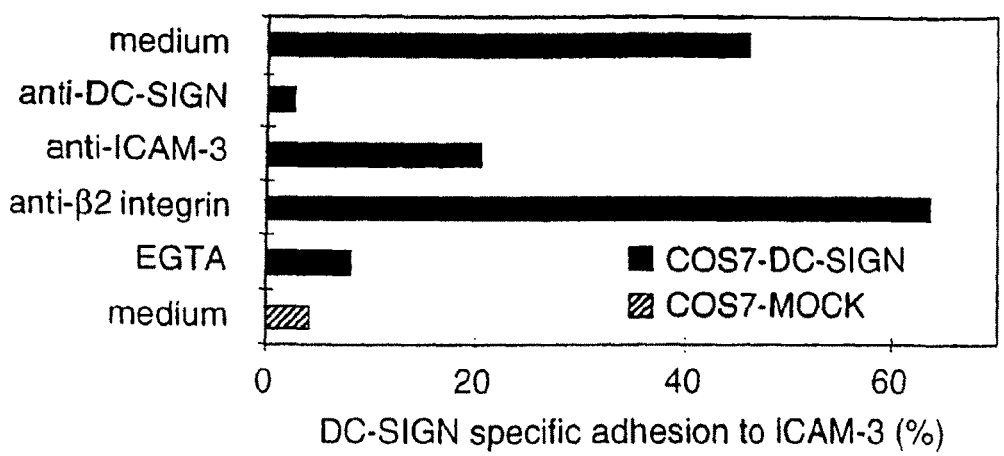

About 30% of the transfected COS7 cells are stained with anti-DC-SIGN-antibody and therefore express DC-SIGN. Moreover, the COS7-DC-SIGN cells are able to bind ICAM-3 whereas mock transfected COS7 cells are unable to bind ICAM-3 (FIG. 4B). Binding of DC-SIGN expressed by COS7 could be completely inhibited by antibodies against ICAM-3 and DC-SIGN, and was $Ca^{2+}$ dependent since EGTA blocks adhesion completely (FIG. 4B).

It as concluded that the ICAM-3 binding receptor expressed by DC (DC-SIGN) is identical to the placenta HIV gp120 binding C-type lectin (Curtis et al., 1992), a type II transmembrane protein consisting of 404 aa with three distinct domains. The N-terminal cytoplasmic domain of 40 aa residues is separated by a hydrophobic stretch of 15 aa from a region which consists of seven complete and one incomplete tandem repeat of nearly identical sequence. The remaining C-terminal region (Cys253-Ala404) shows homology to $Ca^{2+}$-dependent (C-type) lectins (FIG. 3B).

Example 5

DC-SIGN is Specifically Expressed by DC

Flowcytometric analysis of an extensive panel of hematopoietic cells with the AZN-D1/D2 antibodies demonstrates that the antigen is preferentially expressed by DC (Table 1). All the hematopoietic cells tested were negative for DC-SIGN expression except for DC. Furthermore, a RT-PCR analysis confirms that the mRNA encoding DC-SIGN is specifically transcribed in DC which is in accordance with the expression pattern of the DC-SIGN protein (Table 1).

To further investigate the expression of DC-SIGN in vivo, immunohistochemical analysis of secondary lymphoid tissues with the anti-DC-SIGN antibodies was performed. These tissues are known to contain dendritic cells. Sections of tonsils and lymph nodes contained DC-SIGN expressing cells, which were predominantly observed in the T cell area of both tonsils and lymph nodes (FIGS. 5A-D). FIGS. 5A-D show the tissue distribution of DC-SIGN: Immunohistochemical analysis of the expression of DC-SIGN in tonsils and lymph node sections (OMx100). Sections were fixed with acetone and the nuclear staining was performed with Hematein. Staining of DC-SIGN was performed with AZN-D1. The germinal center (GC), T-(T) and B-cell (B) areas are depicted.

Figure 5:
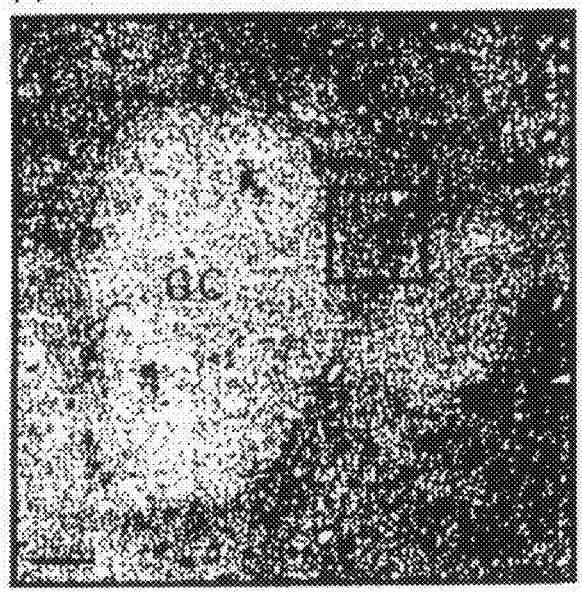
Figure 5:
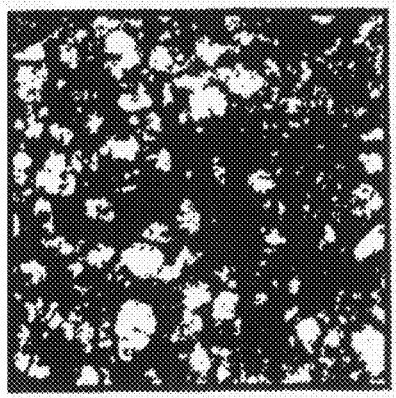
Figure 5:
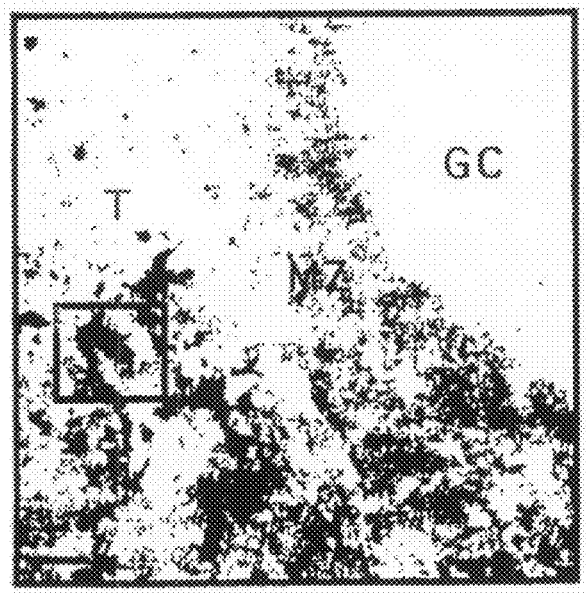
Figure 5:
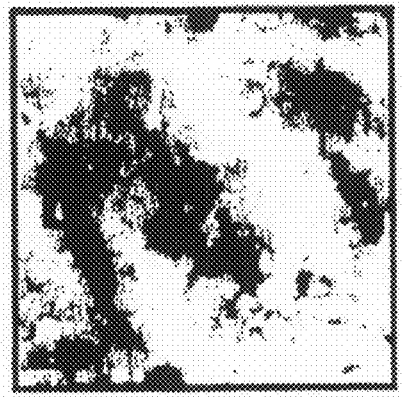

Consistent with the distribution and morphology of dendritic cells, DC-SIGN expressing cells are not detected in the centres centers and the mantle zone (MZ) of the lymphoid tissues (FIGS. 5A and 5C). Staining of serial sections for CD3 and CD14 confirmed that the DC-SIGN expressing cells are distinct from T cells and monocytes (data not shown) as was also demonstrated by both flowcytometric analysis and RT-PCR of these cells (Table 1).

Example 6

DC-SIGN/ICAM-3 Interactions Mediate Transient DC-T Lymphocyte Clustering

To demonstrate that DC bind to ICAM-3 expressing transfectants in a DC-SIGN dependent manner, the capacity of the leukemic cell line K562 transfected with the cDNA encoding ICAM-3 (K562-ICAM-3) to bind to DC was investigated. As shown in FIG. 6A, DC cluster with K562-ICAM-3 in a DC-SIGN dependent manner, since the interaction can be blocked by anti-DC-SIGN antibodies. No clustering was observed between DC and K562 demonstrating that ICAM-3 is the ligand for DC-SIGN. FIGS. 6A-D show that DC-SIGN mediated adhesion of DC to ICAM-3 is involved in the DC-T-lymphocyte interaction:

6A: DC-SIGN mediated adhesion of DC to ICAM-3 is dependent on an intact cytoskeleton. Adhesion of DC to ICAM-3 beads was determined with (open box) or without (filled box) blocking DC-SIGN antibody AZN-D1 in the presence of Cytochalasin D, which was titrated in various concentrations. A representative experiment of 2 experiments is shown (SD<5%).

6B: Heterotypic cell clustering of DC with K562-ICAM-3 cells. K562 and K562 cells stable transfected with the cDNA encoding ICAM-3 (K562-ICAM-3) were labeled with the red dye HE (hydroethidine). DC were labeled with the green dye SFDA. K562 and K562-ICAM-3 were incubated with DC ($50 \times 10^3$ cells/cell type) with or without blocking anti-DC-SIGN antibody (AZN-D1; 10 min. pre-incubation) at 37° C. At different time points the cells were fixed with paraformaldehyde (0.5%) and the heterotypic cell clustering was measured flow-cytometrically. A representative experiment of 2 experiments is given.

6C: Dynamic cell clustering of DC with resting PbL is mediated by DC-SIGN. DC ($50\times10^3$ cells) were pre-incubated with/without the anti-DC-SIGN antibodies AZN-D1 and AZN-D2 (10 µg/ml) for 10 min. at RT. Allogeneic PBL ($1\times10^6$ cells), labeled with the fluorescent dye Calcein-A (25 µg/$10^7$ cells/ml for 30 min. at 37° C.), were added and the cell mixture was incubated at 37° C. The clustering was measured by flow-cytometry. A representative experiment out of 2 is shown.

6D: The DC-SIGN-ICAM-3 interaction is important in DC-induced T-cell proliferation. Allogeneic responder T-lymphocytes ($100\times10^3$) were added to DC-stimulators ($1.5\times10^3$) in the presence of blocking antibodies (20 µ/ml) against LFA-3 (TS2/9) and DC-SIGN (AZN-D1, AZN-D2). The cells were cultured for 4 days. On day 4 the cells were pulsed for 16 h with [$^3$H]methyl-thymidine and the uptake was determined. The results are expressed as the mean percent of CPM from triplicate wells.

DC-SIGN dependent clustering is transient, with a maximum at 60 minutes indicating that DC-SIGN-ICAM-3 interactions may be actively regulated by the DC. Furthermore, this phenomenon allows DC to transiently interact with multiple naive T cells until the interaction is strengthened after TCR engagement.

To test this it was investigated whether clustering of DC to T cells is mediated by DC-SIGN and whether this interaction is also transient. DC were incubated with resting allogeneic T cells (DC:T cell, 1:20) and the DC-T cell clustering was determined. As shown in FIG. 6C, the clustering of DC with T cells is transient and reaches a maximum after 20 min (32%). Furthermore, the DC-T cell interaction can be inhibited (approximately 50%) by anti-DC-SIGN antibodies suggesting that the DC-T cell clustering is also mediated by other surface receptors. Thus, the DC-T cell clustering is indeed transient and partly mediated by DC-SIGN/ICAM-3 interactions. Similarly, FIG. 8 shows that DC-SIGN binds not only with K562 cells expressing cDNA encoding ICAM-3, but also to K562 cells expressing cDNA encoding ICAM-2, and that said binding can be inhibited by both mannan as well as anti DC-SIGN antibodies.

Example 7

Proliferation of Resting T Cells Induced by Allogeneic DC is DC-SIGN Dependent

As DC-SIGN binding to ICAM-3 is important for the clustering of DC with T cells, the role of DC-SIGN in DC induced T cell proliferation was also investigated. Resting T lymphocytes were stimulated with allogeneic DC in the presence or absence of the blocking anti-DC-SIGN antibodies. As shown in FIG. 6D, the anti-DC-SIGN antibodies AZN-D1 and AZN-D2 both inhibited the T-lymphocyte proliferation for more than 75%. Similarly, antibodies against the costimulatory molecule LFA-3, which binds to CD2 on T cells and is also known to mediate T cell proliferation, inhibit T cell proliferation. A combination of anti-LFA-3 and anti-DC-SIGN antibodies completely inhibits T-cell proliferation (FIG. 6D).

Example 8

DC-SIGN is Involved in the HIV-1 Infection of DC

As it was demonstrated hereinabove that DC-SIGN is identical to the placenta HIV gp120 binding lectin and is abundantly expressed by DC, DC-SIGN might facilitate HIV-1 entry into DC. To investigate this, DC was pulsed with HIV-1 and productive infection in DC-T cell co-cultures was measured. DC harvested after 7 days of culture in the presence of IL-4 and GM-CSF expressed low levels of CD4 (Blauvelt et al., 1997; Granelli-Piperno et al., J Exp Med 184(6), 2433-8, 1996) and high levels of DC-SIGN (FIG. 7). As shown in FIG. 7 a strong productive infection takes place when DC are pulsed with HIV-1 for 2 hours, washed and cultured in the presence of activated PBMC cells. By day 3 of the DC-T cell co-culture the p24 Gag protein, a measure for HIV-1 replication, starts to accumulate in the medium (FIG. 7) demonstrating that HIV-1 is efficiently replicated in the co-culture, similar as has been shown by others (Blauvelt et al., 1997; Granelli-Piperno et al., 1998; Granelli-Piperno et al. Curr Biol 9(1), 21-29, 1999). However, when DC prior to the HIV-1 pulse are pre-incubated with anti-DC-SIGN antibodies and incubated with activated PBMC, HIV-1 replication is inhibited for more than 75%, as shown at day 3 and 5 of DC-T cell co-culture (FIG. 7). When DC were incubated with anti-DC-SIGN antibodies after pulsing with HIV-1, efficient HIV-1 replication was still observed in the DC-T cell co-culture (FIG. 7). These findings demonstrate that anti-DC-SIGN antibodies block HIV-1 infection through inhibition of HIV-1 binding to DC and not the HIV-1 transmission from DC to T cells, indicating that DC-SIGN act as a major receptor for HIV-1 on DC. Thus, DC-SIGN is highly expressed on DC and functions as a DC specific receptor for both ICAM-3 and HIV-1.

From the above experimental results, it can inter alia be concluded that the initial interaction of DC with T lymphocytes is antigen-independent and transient. This transient nature provides DC with the capacity to interact with a multitude of T cells until a productive TCR engagement is made. Until now, the mechanism by which this transient process is initiated has been unclear. Herein, it is demonstrated that the interaction of a novel DC specific receptor, DC-SIGN, with ICAM-3 mediates this transient DC-T cell interaction. DC-SIGN is abundantly expressed by DC and it was shown that DC-SIGN serves as a major HIV-1 receptor on DC.

An important role for DC during the course of HIV-1 infection is the ability to spread HIV-1 to T cells, promoting extensive replication that leads to the death of CD4+ T cells (Cameron et al., 1992; Cameron: AIDS Res Hum Retroviruses 10(1), 61-71, 1994). Productive HIV-1 infection of DC has been clearly demonstrated and depends on the development stage of the DC (Granelli-Piperno et al., 1998). Immature DC, cultured from monocytes in the presence of IL-4 and GM-CSF, are productively infected by M-tropic HIV-1 strains (Granelli-Piperno et al., 1996; Granelli-Piperno et al., 1998) (Blauvelt et al., 1997) whereas, both M- and T-tropic HIV-1 entry into mature DC does not lead to a productive infection (Granelli 1998). However, HIV-1 entry into both types of DC does lead to an explosive replication upon co-culturing with either resting or activated T cells (Granelli 1998, 1999). The initial events in HIV-1 infection of target cells include receptor binding and membrane fusion. This process is initiated by the high affinity binding of the envelope glycoprotein gp120 to CD4. However, CD4 alone is not sufficient to initiate fusion, chemokine receptors such as CCR5 and CXCR4 are required as co-receptors for the final fusion event to occur (reviewed by Littman et al., 1998) (Dragic et al., Nature 381(6584), 667-73, 1996; Feng et al., Science 272(5263), 872-7, 1996). DC express low amounts of CD4 whereas high levels of DC-SIGN are expressed on the cell surface. It has been suggested that productive infection of DC and its ability to capture and subsequently transmit HIV-1 are mediated through separate pathways. Productive infection of DC is mediated by a CD4-dependent pathway whereas HIV-1 can be captured by DC through a CD4-independent pathway which still enables DC to transmit HIV-1 to T cells (Blauvelt et al. (1997)). Herein, it was shown that DC-SIGN specifically mediates entry of HIV-1 into DC, as was measured by lack of productive infection in the DC-T cell co-culture upon preincubation of DC with anti-DC-SIGN antibodies prior to the HIV-1 pulse. Anti-DC-SIGN antibodies do not completely inhibit HIV-1 entry into DC. This DC-SIGN-independent pathway is probably mediated by CD4 ( ) which is expressed at low levels on DC. These results confirm the presence of both a CD4-dependent and independent pathway for viral entry into DC. Various adhesion molecules have been shown to be able to inhibit transmission of HIV-1 from DC to T cells through interference of DC-T cell contact (Tsunetsugu-Yokota et al., 1997). Anti-DC-SIGN antibodies could not prevent HIV-1 transmission to T cells when anti-DC-SIGN antibodies were added after the HIV-1 pulse to inhibit the DC-T cell interaction. These data indicate that DC-SIGN serves as a major receptor for HIV-1 entry into DC. The fact that DC express high levels of DC-SIGN and low levels of CD4 FIG. 7) further demonstrates that HIV-1 entry into DC is predominantly mediated by DC-SIGN. The discovery of DC-SIGN as a HIV-1 receptor could be important in a better understanding of HIV-1 entry into DC. Furthermore, the inhibition of HIV-1 infection observed in the presence of anti-DC-SIGN antibodies will enable the development of anti-DC-SIGN antibodies in therapeutic strategies against viral infection and regional spread of HIV-1.

DC constitute an heterologous population of cells which are present at trace levels in various tissues. To better define the different populations a lot of effort has gone into the generation of antibodies that are directed against DC lineage specific cell surface molecules. So fat only a few antibodies have been generated which recognize human DC specific antigens ((Hock et al., Immunol. 83, 573-581, 1994), (de Saint-Vis et al., Immunity 9(3), 325-36, 1998)(Hart et al., 1997). DC-SIGN can now been added to this list of human DC specific antigens since it was demonstrated herein that at the protein as well as mRNA level, of all hematopoietic cells tested, only DC express DC-SIGN (Table 1). In situ DC-SIGN is exclusively expressed by DC subsets present in the T cell area of tonsils and lymph nodes. These mature DC are very potent in the activation of naive T cells. Therefore, DC-SIGN expression in situ correlates with its function as an important mediator of DC-T cell clustering and subsequent T cell activation.

Activation of resting T lymphocytes by antigen presenting cells is a critically important step in the acquired immune response. Located in most tissues, DC capture and process antigens, and migrate to lymphoid tissues where they interact with and activate naive antigen-specific T cells. T cells are directed by chemokines to these sites of antigen presentation. Recently, a DC specific chemokine DC-CK1 was identified which specifically attracts naive T cells to immune initiation sites (Adema et al., Nature 387, 713-717, 1997). Upon arrival in secondary lymphoid tissues, T cells interact with DC and activation occurs after TCR recognition of peptides bound to MHC molecules. However, since the affinity of the TCR for the antigen presented by MHC molecules is very low and the number of specific MHC-peptide complexes on APC is limited, the interaction of TCR with antigen is usually insufficient to drive the formation of intimate membrane contact between DC and T-lymphocyte necessary for full activation.

To date LFA-1 was the most important receptor for ICAM-3 on DC. However, its role in ICAM-3 binding has now become disputable due to the discovery herein of DC-SIGN. It was demonstrated that adhesion of DC to ICAM-3 is completely mediated by DC-SIGN. DC-SIGN is more abundantly expressed by DC than LFA-1 (FIG. 2B). Furthermore, LFA-1 is inactive on DC (FIG. 2C) and its affinity for ICAM-3 is much lower than that of DC-SIGN for ICAM-3. These data clearly demonstrate that DC-SIGN is the primary receptor for ICAM-3 on DC. The function for DC-SIGN on DC was farther clarified by the finding that anti-DC-SIGN antibodies partially inhibited transient DC-T cell clustering. Therefore, DC-SIGN is involved in the initial DC-T cell interaction in the immune response. A role which was previously attributed to LFA-1. The transient nature of the DC-T cell interaction mediated by DC-SIGN enables DC to interact with a large number of resting T cells, until a productive TCR mediated interaction is made upon which the interaction is stabilized. The importance of the DC-SIGN-ICAM-3 interaction is further underscored by the finding that antibodies against DC-SIGN are able to inhibit allogeneic DC induced T-lymphocyte proliferation. Moreover, the combination of antibodies against DC-SIGN and LFA-3, a known co-stimulatory molecule ( ), almost completely inhibit T-lymphocyte proliferation. Therefore, transient high affinity adhesion of DC-SIGN to ICAM-3 plays an important role in the initial antigen-independent interaction between DC and naive T cells. Presumably, this initial high affinity interaction enables engagement of the TCR by the antigen bound to the MHC, which subsequently initiates several other adhesive interactions between DC and T cells, such as the LFA-1-ICAM-1 interaction. Since LFA-1 is inactive on T cells, activation of the TCR/CD3 complex after antigen presentation by DC will result in activation of LFA-1 and subsequent strong binding of LFA-1 to ICAM-1 expressed on DC ( ). Strengthening of the interaction between DC and T cell via multiple contacts will then lead to full activation of the T lymphocyte by the DC stimulator ( ).

In conclusion, a novel ICAM-3 receptor on DC was identified, designated DC-SIGN, which receptor is specifically expressed by human DC and is involved in the initial transient DC-T cell interaction necessary for initiating an immune response. Interestingly, DC-SIGN is also able to bind the HIV envelope protein gp120 and to facilitate HIV-1 entry into DC. Various therapeutic and profylactic possibilities and techniques, based upon the findings disclosed herein, will suggest themselves to the skilled person.

Example 9

Experimental Procedures

Ex. 9A

Antibodies

The following antibodies were used: KIM185 (anti-β2 integrin, (Andrew et al., Eur. J. Immunol. 23, 2217-2222, 1993), AZN-L19 (anti-β2 integrin), NKI-L15 (anti-αL, (Keizer et al., Eur. J. Immunol. 15, 1142-1147, 1985)), AIIB2 (anti-β1 integrin, (Da Silva et al., J. Immunol. 143, 617-622, 1989)), CBR-IC3/1 and CBR-IC3/2 (anti-ICAM-3 (de Fougerolles et al., J. Exp. Med. 177, 1187-1192, 1993)), CD14

(WT14 ( )), CD4 (wt4 ( )). The anti-DC-SIGN antibodies AZN-D1 and AZN-D2 were obtained by immunizing BALB/c mice with DC and subsequently screening the hybridoma supernatants for the ability to block adhesion of DC to ICAM-3 as measured by the fluorescent beads adhesion assay.

Ex. 9B

Cells

DC were cultured from monocytes as described (Sallusto and Lanzavecchia, J. Exp. Med. 179, 1109-1118, 1994; Romani et al., J. Exp. Med. 180, 83-93, 1994). Briefly, monocytes were isolated from fresh PBMC by an adherence step. The monocytes were cultured in the presence of IL-4 (Schering-Plough, Brussels, Belgium; 500 U/ml) and GM-CSF (Schering-Plough, Brussels, Belgium; 1000 U/ml) for 7 days. At day 4 fresh cytokines were added. At day 7 the phenotype of the cultured DC was confirmed by flowcytometric analysis of the expression of MHC class I and II, CD1a, p150,95 and CD80. Stable K562 transfectants expressing ICAM-3 (K562-ICAM-3) were generated by transfection of K562 with 10 μg PCRII ICAM-3 R1 plasmid (gift from Dr D. Simmons) and 2 μg PGK-hyg vector (te Riele et al 1990) by electroporation as described (Lub et al., Mol. Biol Cell 8, 719-728, 1997). Resting T cells (>90% CD3 positive) were obtained by centrifugal elutriation of PBMC from bone marrow of healthy donors, as described (Figdor et al., J. Immunol. Methods 68, 73-87, 1984).

Ex. 9C

Radiolabeling, Immunoprecipitation and Protein Sequence Analysis

Cells were surface labeled with $Na^{125}I$ (Habersham, Buckinghamshire, UK) through the lactoperoxidase method (Pink and Ziegler, 1979, in: *Research Methods in Immunology*, L. Lefkovits and B. Pernis, eds. (New York: Academic Pres), pp. 169-180.). DC were lysed for 1 hr at 4° C. in lysis buffer (1% NP40, 50 mM tri-ethanolamine (pH 7.8), 150 mM NaCl, 1 mM CaCl, 1 mM $MgCl_2$, 1 mM PMSF, 0.02 mg/ml leupeptin). Nuclear debris was removed from the lysate by centrifugation at 13,000 g for 15 min at 4° C. Pre-cleared lysates were incubated for 3 hr with a specific mAb covalently coupled to Protein A sepharose CL-4B beads (Pharmacia Fine Chemicals, Piscataway, N.J.). The immunoprecipitates were extensively washed with lysis buffer and analysed by SDS-PAGE according to a modification of the Laemmli procedure (Laemmli, Nature 227, 680-685, 1970). Tryptic digestion of the excised protein, purification of the resulting peptides and sequence analysis was performed by Eurosequence BV (Groningen, The Netherlands).

Ex. 9D

Isolation and Expression of the cDNA Encoding DC-SIGN

Total RNA was isolated by an acidic guanidinium isothiocyanate-phenol-chloroform procedure (Chomczynski and Sacchi, Anal Biochem 162(1), 156-9, 1987). The cDNA encoding the placenta gp120 binding C-type lectin was amplified by RT-PCR on total RNA from DC. PCR primers were based on the nucleotide sequence of the placenta gp120 binding C-type lectin (accession no. M98457, (Curtis et al., 1992)) and the nucleotide sequences (5' to 3') are as follows: XF29, AGAGTGGGGTGACATGAGTG (SEQ ID NO:3); XR1265, GAAGTTCTGCTACGCAGGAG (SEQ ID NO:4). The PCR fragment was cloned into the pGEM-T vector (Promega, Madison, Wis.) and sequenced. The nucleotide sequence of the cloned cDNA was identical to that of placenta gp120 binding C-type lectin (Curtis et al., 1992). The cDNA was subsequently cloned into the eukaryotic expression vector pRc/CMV (pRc/CMV-DC-SIGN) and COST cells were transient transfected with pRc/CMV-DC-SIGN using the DEAE dextran method (Seed and Aruffo, Proc. Natl. Acad. Sci. U.S.A. 84, 3365-3369, 1987).

Ex. 9E

Fluorescent Beads Adhesion Assay

Carboxylate-modified TransFluorSpheres (488/645 nm, 1.0 μm; Molecular Probes, Eugene, Oreg.) were coated with ICAM-1 Fc and ICAM-3 Fc as described previously (Geijtenbeek et al., 1999 submitted). Briefly, 20 μl streptavidin (5 mg/ml in 50 mM MES-buffer) was added to 50 μl TransFluorSpheres. 30 μl EDAC (1.33 mg/ml) was added and the mixture was incubated at RT for 2 h. The reaction was stopped by the addition of glycin to a final concentration of 100 mM. The streptavidin-coated beads were washed three times with PBS (50 mM phosphate, 0.9% NaCl pH 7.4) and resuspended in 150 μl PBS, 0.5% BSA (w/v). The streptavidin-coated beads (15 μl) were incubated with biotinylated goat-anti-human anti-Fc Fab2 fragments (6 μg/ml) in 0.5 ml PBA for 2 hours at 37° C. The beads were washed once with PBS, 0.5% BSA and incubated with human IgG1 Fc fused ligands (ICAM-1 Fc, VCAM-1 Fc; 250 ng/ml) in 0.5 ml overnight at 4° C. The ligand-coated beads were washed, resuspended in 100 μl PBS, 0.5% BSA and stored at 4° C. ICAM-1 Fc and ICAM-3 Fc consist of the extracellular part of the protein fused to a human IgG1 Fe fragment (provided by Dr D. Simmons). The fluorescent beads adhesion assay was performed as described by Geijtenbeek et al. (submitted). Briefly, cells were resuspended in Tris-Sodium-BSA buffer (20 mM Tris-HCl pH 8.0, 150 mM NaCl, 1 mM $CaCl_2$, 2 mM $MgCl_2$, 0.5% BSA; $5 \times 10^6$ cells/ml). 50.000 cells were pre-incubated with/without blocking mAb (20 μg/ml) for 10 min at RT in a 96-wells V-shaped bottom plate. Ligand-coated fluorescent beads (20 beads/cell) and different stimuli/inhibitors were added and the suspension was incubated for 30 min at 37° C. The cells were washed and resuspended in 100 μl TSA. Adhesion was determined by measuring the percentage of cells, which have bound fluorescent beads, by flowcytometry using the FACScan (Becton and Dickinson & Co., Oxnard, Calif.).

Ex. 9F

Heterotypic Cell Clustering Assays

Clustering between DC and ICAM-3 expressing cells was assessed by flowcytometry. DC and ICAM-3 expressing cells ($2 \times 10^6$ cells/ml) were labeled respectively with sulfofluorescein (Molecular Probes, Eugene, Ore.; 50 μg/ml) and hydroethidine (Molecular Probes, Eugene, Oreg.; 40 μg/ml) for 1 hour at 37° C. After washing, DC and the ICAM-3 expressing cells were mixed ($50 \times 10^3$ cells each) and incubated at 37° C. At different time points the cells were fixed with paraformaldehyde (0.5%) and the heterotypic cell clustering was measured by flowcytometry using the FACScan (Becton and Dickinson & Co., Oxnard, Calif.).

Clustering between DC with resting T cells was assessed by a different method. DC (50×10³ cells) were pre-incubated with/without the anti-DC-SIGN antibodies AZN-D1 and AZN-D2 (10 g/ml) for 10 min. at RT. Allogeneic PBL (1×10⁶ cells), labeled with the fluorescent dye Calcein-A (Molecular Probes, Eugene, Oreg.; 25 µg/10⁷ cells/ml for 30 min. at 37°), were added and the cell mixture was incubated at 37° C. The clustering was determined by measuring percentage of DC which have bound fluorescent T cells by flowcytometry using the FACScan (Becton and Dickinson & Co., Oxnard, Calif.).

Ex. 9G

DC-Induced T Cell Proliferation Assay

Allogeneic responder T-lymphocytes (100×10³) were added to DC-stimulators (1.5×10³) in the presence of blocking antibodies (20 _g/ml). The cells were cultured for 4 days. On day 4 the cells were pulsed for 16 h with [³H]methyl-thymidine (1.52 TBq/mmol, 0.5 µCi/well; Amersham, Buckinghamshire, UK) and the uptake was quantified.

Ex. 9H

HIV-1 Infection of DC

HIV-1$_{Ba\text{-}L}$ was grown to high titer in monocyte-derived macrophages (MDM). Seven days after titration of the virus stock on MDM, TCID$_{50}$ was determined with a p24 antigen ELISA ((Diagnostics Pasteur, Marnes la Coquette, France) and estimated as 10⁴/ml. DC (50×10³), pre-incubated with antibodies (50 µg/ml) for 20 min. at RT, were pulsed for 2 h. with wild-type HIV-1$_{Ba\text{-}L}$ (at a multiplicity of infection of 10³ infectious units per 10⁵ cells), washed and co-cultured with PHA/IL-2 activated PBMC (50×10³). Supernatants were collected 3 and 5 days after DC-T cell co-culture and p24 antigen levels were measured by a p24 antigen ELISA (Diagnostics Pasteur, Marnes la Coquette, France). PBMC were activated by culturing them in the presence of IL-2 (10 U/ml) and PHA (10 µg/ml).

Ex. 9I

Immunohistochemical Analysis

Cryosections (8 µm) of tonsils and lymph nodes were fixated in 100% aceton (10 min), washed with PBS and incubated with the first antibody (10 µl/ml) for 60 min at RT. After washing, the final staining was performed with the ABC-AP Vectastain kit (Vector Laboratories, Burlingame, Calif.) according to the manufacturer's protocol. Nuclear staining was performed with hematein ( ).

TABLE 1

Expression level of DC-SIGN on hematopoietic cells as determined by flowcytometric analyses and RT-PCR.

| Cell-type | DC-SIGN expression* | DC-SIGN mRNA‡ |
|---|---|---|
| monocytes | − | − |
| DC day 7 | +++ | + |
| PBL | − | − |
| T cells | − | − |
| B cells | − | − |
| B-cells (tonsils)$ | − | n.d. |
| Thymocytes | − | − |
| Granulocytes | − | − |
| CD34+ cells | − | n.d. |
| PBMC (activated#) | − | − |
| T cell lines† | − | − |
| monocytic cell lines†† | − | − |

*mean fluorescence: − = <20, +++ >400 (staining with AZN-D1)
‡RT-PCR with the DC-SIGN specific primers XF29 and XR1265 on total RNA isolated from the different cells
$isolated from tonsils
activated with PHA (10 µg/ml) and IL-2 (10 U/ml) for 2 days
†T cell lines: HSB, PEER, CEM and Jurkat
††monocytic cell lines: THP-1, MM6 and U937
n.d., not determined

---

The invention claimed is:

1. A conjugate molecule comprising: an antigen attached to an antibody, or an antigen binding fragment of an antibody, that binds to a protein with the amino acid sequence of SEQ ID NO: 2 (DC-SIGN) on the surface of a dendritic cell.

2. The conjugate molecule of claim 1, wherein said antibody is a monoclonal antibody.

3. The conjugate molecule of claim 1, wherein said antigen binding fragment is a F(ab)$_2$, Fab', Fab, or Fv fragment.

4. The conjugate molecule of claim 2, wherein said antibody is selected from the group consisting of: i) an antibody produced by hybridoma ECACC accession number 99040818 and ii) an antibody produced by hybridoma ECACC accession number 99040819.

5. The conjugate molecule of claim 1, wherein said antigen is attached to said antibody, or an antigen binding fragment of said antibody, by a) covalent binding, b) ligand-ligand interaction, c) complexing, d) ligation, or e) expression of a fusion protein comprising said antigen and said compound.

6. The conjugate molecule of claim 1, wherein the antigen is a cancer antigen.

7. The conjugate molecule of claim 6, wherein the cancer antigen is selected from the group consisting of gp 100, g250, p53, MAGE, BAGE, GAGE, MART 1, Tyrosinase related protein II, and Tyrosinase related protein.

8. The conjugate molecule of claim 1, wherein the antigen is an antigen from an infectious micro-organism.

9. The conjugate molecule of claim 8, wherein the micro-organism causes influenza, mumps, measles, rubella, diphtheria, or tetanus.

10. The conjugate molecule of claim 8, wherein the antigen is selected from the group consisting of Haemophilus influenzae, Neisseria, Bordetella pertussis, Polyomyletus, Pneumococcus, HIV, and Herpes Simplex virus.

11. A pharmaceutical composition comprising the conjugate molecule of claim 1.

12. A composition comprising the conjugate molecule of claim 1 and at least one pharmaceutically acceptable carrier, excipient, adjuvant or formulant.

* * * * *

UNITED STATES PATENT AND TRADEMARK OFFICE
CERTIFICATE OF CORRECTION

PATENT NO. : 8,058,400 B2  
APPLICATION NO. : 11/977151  
DATED : November 15, 2011  
INVENTOR(S) : Figdor et al.

Page 1 of 1

It is certified that error appears in the above-identified patent and that said Letters Patent is hereby corrected as shown below:

On the Title Page

Related U.S. Application Data

Item (62) please replace "Division of application No. 10/625,204, filed on Jul. 23, 2003, now Pat. No. 7,285,642" with --Continuation of application No. 10/625,204, filed on Jul. 23, 2003, now Pat. No. 7,285,642; which is a Division of application No. 09/719,961, filed on September 24, 2001, now Pat. No. 7,148,329, which is a National Stage Entry of PCT/NL00/00253, filed on April 19, 2000, which claims the benefit of application No. 60,176,924, filed January 20, 2000--

Insert Item --(30) Foreign Application Priority Data

Apr. 19, 1999 (EP) .......................... 99201204--

Signed and Sealed this  
Seventh Day of August, 2012

David J. Kappos  
*Director of the United States Patent and Trademark Office*

SEQUENCE LISTING

```
<160> NUMBER OF SEQ ID NOS: 6

<210> SEQ ID NO 1
<211> LENGTH: 1215
<212> TYPE: DNA
<213> ORGANISM: Homo sapiens
<220> FEATURE:
<221> NAME/KEY: CDS
<222> LOCATION: (1)..(1215)

<400> SEQUENCE: 1 atg agt gac tcc aag gaa cca aga ctg cag cag ctg ggc ctc ctg gag     48
Met Ser Asp Ser Lys Glu Pro Arg Leu Gln Gln Leu Gly Leu Leu Glu
1               5                   10                  15 gag gaa cag ctg aga ggc ctt gga ttc cga cag act cga gga tac aag     96
Glu Glu Gln Leu Arg Gly Leu Gly Phe Arg Gln Thr Arg Gly Tyr Lys
            20                  25                  30 agc tta gca ggg tgt ctt ggc cat ggt ccc ctg gtg ctg caa ctc ctc    144
Ser Leu Ala Gly Cys Leu Gly His Gly Pro Leu Val Leu Gln Leu Leu
        35                  40                  45
```

| | | |
|---|---|---|
| tcc ttc acg ctc ttg gct ggg ctc ctt gtc caa gtc tcc aag gtc ccc<br>Ser Phe Thr Leu Leu Ala Gly Leu Leu Val Gln Val Ser Lys Val Pro<br>50                          55                         60 | | 192 |
| agc tcc ata agt cag gaa caa tcc agg caa gac gcg atc tac cag aac<br>Ser Ser Ile Ser Gln Glu Gln Ser Arg Gln Asp Ala Ile Tyr Gln Asn<br>65                        70                     75                     80 | | 240 |
| ctg acc cag ctt aaa gct gca gtg ggt gag ctc tca gag aaa tcc aag<br>Leu Thr Gln Leu Lys Ala Ala Val Gly Glu Leu Ser Glu Lys Ser Lys<br>                     85                     90                     95 | | 288 |
| ctg cag gag atc tac cag gag ctg acc cag ctg aag gct gca gtg ggt<br>Leu Gln Glu Ile Tyr Gln Glu Leu Thr Gln Leu Lys Ala Ala Val Gly<br>                  100                     105                    110 | | 336 |
| gag ctt cca gag aaa tct aag ctg cag gag atc tac cag gag ctg acc<br>Glu Leu Pro Glu Lys Ser Lys Leu Gln Glu Ile Tyr Gln Glu Leu Thr<br>        115                     120                    125 | | 384 |
| cgg ctg aag gct gca gtg ggt gag ctt cca gag aaa tct aag ctg cag<br>Arg Leu Lys Ala Ala Val Gly Glu Leu Pro Glu Lys Ser Lys Leu Gln<br>130                        135                    140 | | 432 |
| gag atc tac cag gag ctg acc tgg ctg aag gct gca gtg ggt gag ctt<br>Glu Ile Tyr Gln Glu Leu Thr Trp Leu Lys Ala Ala Val Gly Glu Leu<br>145                        150                    155                  160 | | 480 |
| cca gag aaa tct aag atg cag gag atc tac cag gag ctg act cgg ctg<br>Pro Glu Lys Ser Lys Met Gln Glu Ile Tyr Gln Glu Leu Thr Arg Leu<br>                  165                     170                    175 | | 528 |
| aag gct gca gtg ggt gag ctt cca gag aaa tct aag cag cag gag atc<br>Lys Ala Ala Val Gly Glu Leu Pro Glu Lys Ser Lys Gln Gln Glu Ile<br>                  180                     185                    190 | | 576 |
| tac cag gag ctg acc cgg ctg aag gct gca gtg ggt gag ctt cca gag<br>Tyr Gln Glu Leu Thr Arg Leu Lys Ala Ala Val Gly Glu Leu Pro Glu<br>                  195                     200                    205 | | 624 |
| aaa tct aag cag cag gag atc tac cag gag ctg acc cgg ctg aag gct<br>Lys Ser Lys Gln Gln Glu Ile Tyr Gln Glu Leu Thr Arg Leu Lys Ala<br>210                        215                    220 | | 672 |
| gca gtg ggt gag ctt cca gag aaa tct aag cag cag gag atc tac cag<br>Ala Val Gly Glu Leu Pro Glu Lys Ser Lys Gln Gln Glu Ile Tyr Gln<br>225                        230                    235                    240 | | 720 |
| gag ctg acc cag ctg aag gct gca gtg gaa cgc ctg tgc cac ccc tgt<br>Glu Leu Thr Gln Leu Lys Ala Ala Val Glu Arg Leu Cys His Pro Cys<br>                  245                     250                    255 | | 768 |
| ccc tgg gaa tgg aca ttc ttc caa gga aac tgt tac ttc atg tct aac<br>Pro Trp Glu Trp Thr Phe Phe Gln Gly Asn Cys Tyr Phe Met Ser Asn<br>                  260                     265                    270 | | 816 |
| tcc cag cgg aac tgg cac gac tcc atc acc gcc tgc aaa gaa gtg ggg<br>Ser Gln Arg Asn Trp His Asp Ser Ile Thr Ala Cys Lys Glu Val Gly<br>        275                     280                    285 | | 864 |
| gcc cag ctc gtc gta atc aaa agt gct gag gag cag aac ttc cta cag<br>Ala Gln Leu Val Val Ile Lys Ser Ala Glu Glu Gln Asn Phe Leu Gln<br>290                        295                    300 | | 912 |
| ctg cag tct tcc aga agt aac cgc ttc acc tgg atg gga ctt tca gat<br>Leu Gln Ser Ser Arg Ser Asn Arg Phe Thr Trp Met Gly Leu Ser Asp<br>305                        310                    315                    320 | | 960 |
| cta aat cag gaa ggc acg tgg caa tgg gtg gac ggc tca cct ctg ttg<br>Leu Asn Gln Glu Gly Thr Trp Gln Trp Val Asp Gly Ser Pro Leu Leu<br>                  325                     330                    335 | | 1008 |
| ccc agc ttc aag cag tat tgg aac aga gga gag ccc aac aac gtt ggg<br>Pro Ser Phe Lys Gln Tyr Trp Asn Arg Gly Glu Pro Asn Asn Val Gly<br>        340                     345                    350 | | 1056 |
| gag gaa gac tgc gcg gaa ttt agt ggc aat ggc tgg aac gac gac aaa<br>Glu Glu Asp Cys Ala Glu Phe Ser Gly Asn Gly Trp Asn Asp Asp Lys<br>355                        360                    365 | | 1104 |

```
tgt aat ctt gcc aaa ttc tgg atc tgc aaa aag tcc gca gcc tcc tgc      1152
Cys Asn Leu Ala Lys Phe Trp Ile Cys Lys Lys Ser Ala Ala Ser Cys
    370                 375                 380 tcc agg gat gaa gaa cag ttt ctt tct cca gcc cct gcc acc cca aac      1200
Ser Arg Asp Glu Glu Gln Phe Leu Ser Pro Ala Pro Ala Thr Pro Asn
385                 390                 395                 400 ccc cct cct gcg tag                                                  1215
Pro Pro Pro Ala <210> SEQ ID NO 2
<211> LENGTH: 404
<212> TYPE: PRT
<213> ORGANISM: Homo sapiens

<400> SEQUENCE: 2

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
        35                  40                  45

Ser Phe Thr Leu Leu Ala Gly Leu Leu Val Gln Val Ser Lys Val Pro
    50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
    130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
                165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
    210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
                245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
    290                 295                 300

Leu Gln Ser Ser Arg Ser Asn Arg Phe Thr Trp Met Gly Leu Ser Asp
305                 310                 315                 320
```

```
Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
                340                 345                 350

Glu Glu Asp Cys Ala Glu Phe Ser Gly Asn Gly Trp Asn Asp Asp Lys
            355                 360                 365

Cys Asn Leu Ala Lys Phe Trp Ile Cys Lys Lys Ser Ala Ala Ser Cys
        370                 375                 380

Ser Arg Asp Glu Glu Gln Phe Leu Ser Pro Ala Pro Ala Thr Pro Asn
385                 390                 395                 400

Pro Pro Pro Ala

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agagtggggt gacatgagtg                                                20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gaagttctgc tacgcaggag                                                20

<210> SEQ ID NO 5
<211> LENGTH: 11
<212> TYPE: PRT
<213> ORGANISM: Homo sapiens

<400> SEQUENCE: 5

Ser Lys Gln Gln Glu Ile Tyr Gln Glu Leu Thr
1               5                   10

<210> SEQ ID NO 6
<211> LENGTH: 11
<212> TYPE: PRT
<213> ORGANISM: Homo sapiens

<400> SEQUENCE: 6

Ser Ala Glu Glu Gln Asn Phe Leu Gln Leu Gln
1               5                   10
```